United States Patent
Tanaka et al.

(10) Patent No.: US 7,633,061 B2
(45) Date of Patent: Dec. 15, 2009

(54) METHOD AND APPARATUS FOR MEASURING PATTERN DIMENSIONS

(75) Inventors: Maki Tanaka, Yokohama (JP); Chie Shishido, Kawasaki (JP); Wataru Nagatomo, Yokohama (JP)

(73) Assignee: Hitachi High-Technologies Corporation, Tokyo (JP)

( * ) Notice: Subject to any disclaimer, the term of this patent is extended or adjusted under 35 U.S.C. 154(b) by 97 days.

(21) Appl. No.: 12/034,696

(22) Filed: Feb. 21, 2008

(65) Prior Publication Data
US 2008/0197280 A1 Aug. 21, 2008

(30) Foreign Application Priority Data
Feb. 21, 2007 (JP) ............... 2007-040190

(51) Int. Cl.
H01J 37/256 (2006.01)
G01B 15/00 (2006.01)
G03F 9/00 (2006.01)

(52) U.S. Cl. .............. 250/306; 250/307; 250/310; 250/311; 250/492.22; 250/492.2; 430/30; 430/296; 430/942

(58) Field of Classification Search ............ 250/306, 250/307, 310, 311, 492.22, 492.2; 430/30, 430/296, 942
See application file for complete search history.

(56) References Cited

U.S. PATENT DOCUMENTS 6,929,892 B2 * 8/2005 Shishido et al. ............. 430/30

2006/0245636 A1 * 11/2006 Kitamura et al. ............. 382/149

OTHER PUBLICATIONS

Andrew Habermas, et al., 193nm CD Shrinkage Under SEM: Modeling the Mechanism, Proceedings of SPIE vol. 4689 (2002).
J.S. Villarrubia, et al., Scanning Electron Microscope Analog of Scatterometry, Proceedings of SPIE vol. 4689 2002, National Institute of Standard and Technology, Gaithersburg, MD 20899, USA.
Chie Shishido, et al., Does and Focus Estimation Using Top-Down SEM Images, Proceedings of SPIE vol. 5038 2003.
J.S. Villarrubia, et al., A Simulation Study of Repeatability and Bias in the CD-SEM, Proceedings of SPIE vol. 5038 2003, National Institute of Standard and Technology, Gaithersburg, MD 20889, USA.
Atsuko Yamaguchi, et al., Impact of Long-Period Line-Edge Roughness (LER) on Accuracy in CD Measurement, Proc. Of SPEC vol. 5752 (2005), Bellingham, WA.

* cited by examiner

*Primary Examiner*—Nikita Wells
(74) *Attorney, Agent, or Firm*—Antonelli, Terry, Stout & Kraus, LLP.

(57) ABSTRACT

It is difficult for a material having low resistance to electron beam irradiation to obtain an electron microscopic image having a high S/N ratio. A conventional image smoothing process can improve stability of measurement, but this process has a problem of measurement errors for absolute values, reduction of sensitivity, deterioration of quality of cubic shape information and the like. In the present invention, by performing an image averaging process without deteriorating cubic shape information of a signal waveform in consideration of dimension deviation of a measurement target pattern, measurement stability is compatible with improvement of precision and sensitivity. Accordingly, it is possible to realize measurement of pattern dimensions and shapes with high precision and control of a highly sensitive semiconductor manufacturing process using the measurement.

14 Claims, 23 Drawing Sheets

Measurement target pattern

Note: Signal waveform in the below graph is an enlargement of only a left edge.

Present invention

FIG.4A

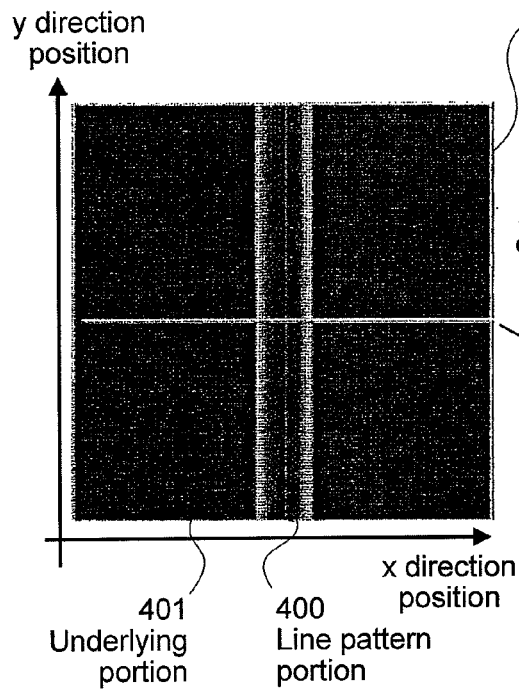

y direction position / x direction position

100 Length-measuring SEM image (ideal image)

401 Underlying portion
400 Line pattern portion

FIG.4B

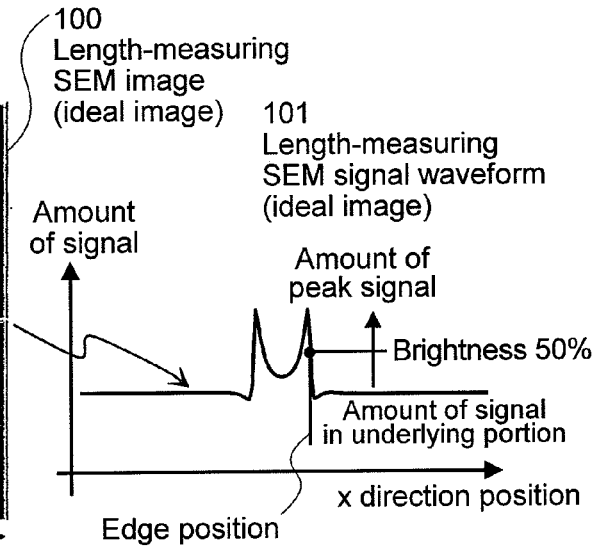

101 Length-measuring SEM signal waveform (ideal image)

Amount of signal / x direction position

Amount of peak signal
Brightness 50%
Amount of signal in underlying portion
Edge position

FIG.4C

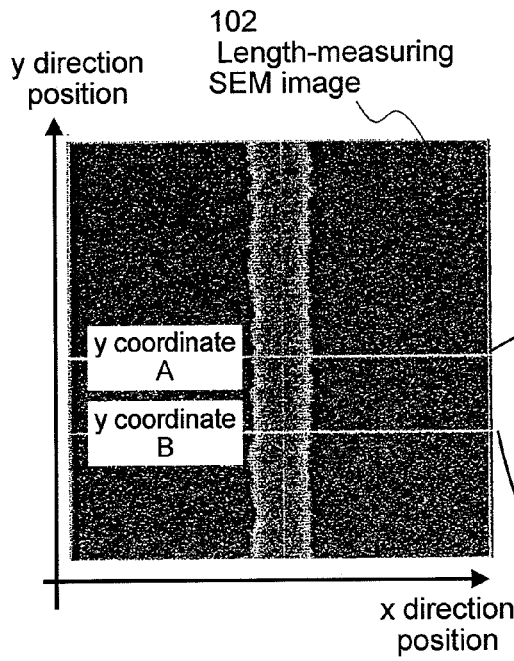

102 Length-measuring SEM image y coordinate A
y coordinate B

FIG.4D

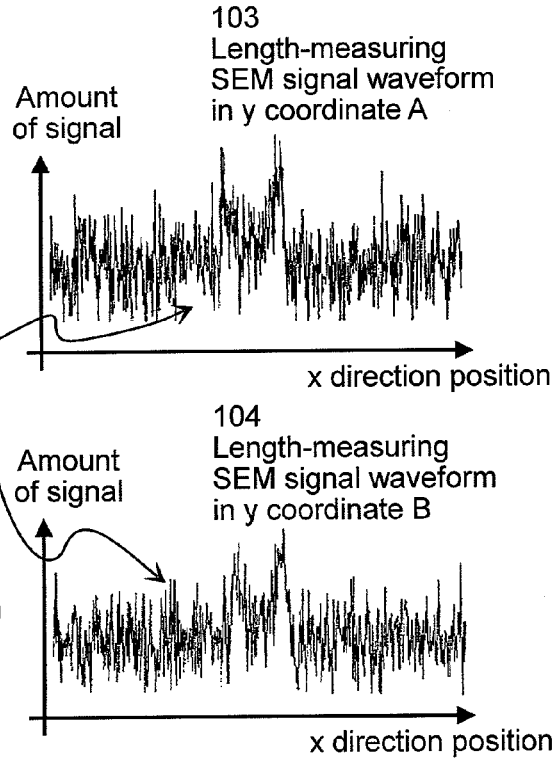

103 Length-measuring SEM signal waveform in y coordinate A

104 Length-measuring SEM signal waveform in y coordinate B

FIG. 7A
Off-line process
FIG. 7B
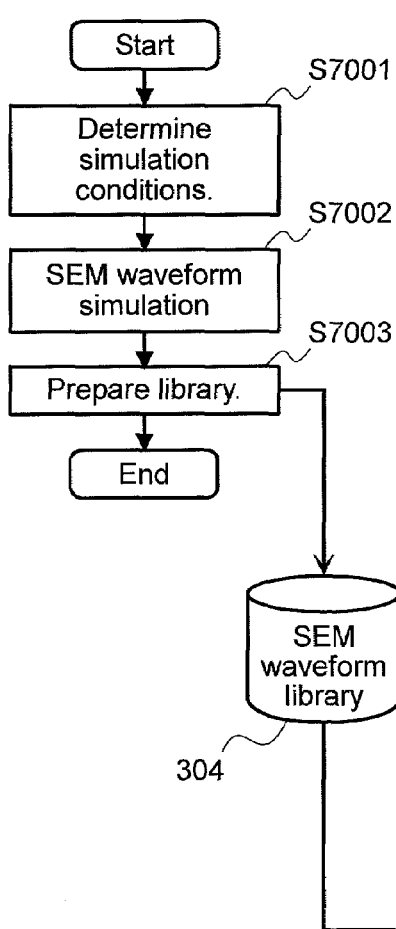
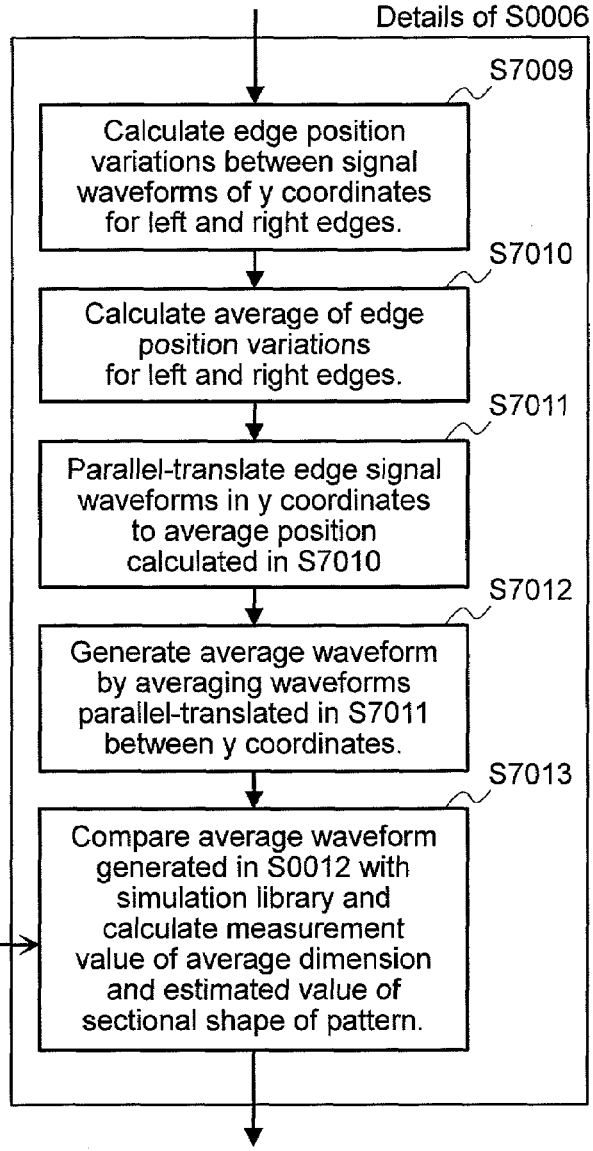

Image features

Database preparation

Exposure apparatus parameter estimation

Relationship between LER-caused CD variation, measured LWR, and power spectrum of LWR.

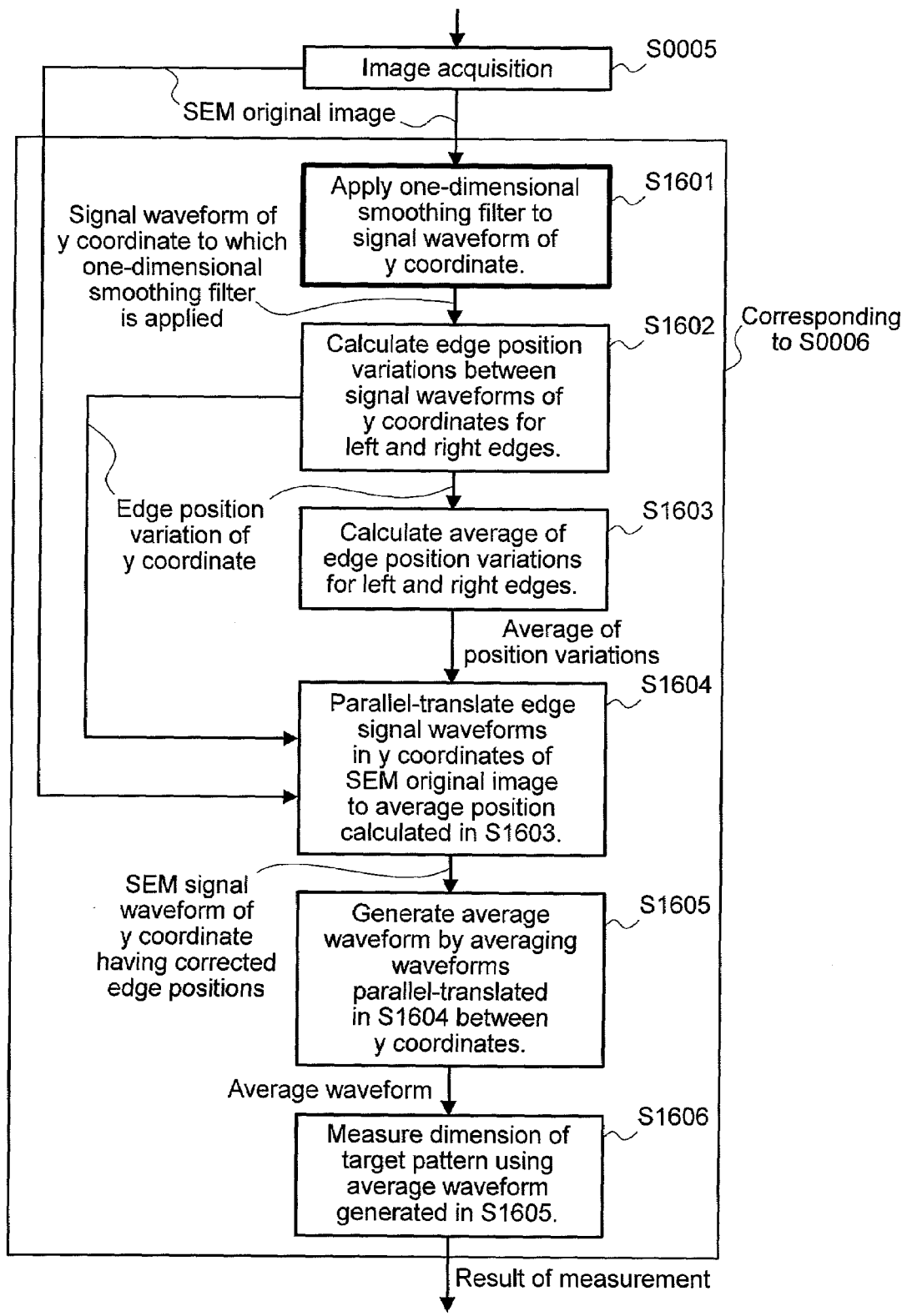

FIG.17A            FIG.17B
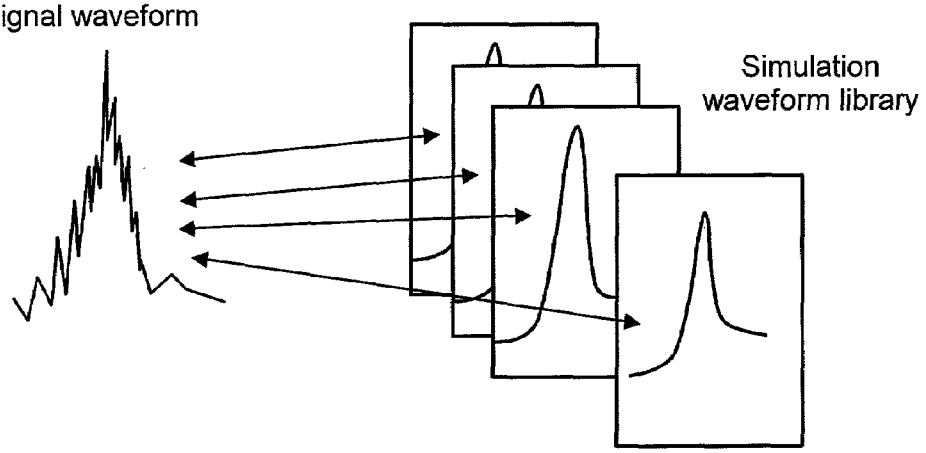
    
FIG.17C            FIG.17D
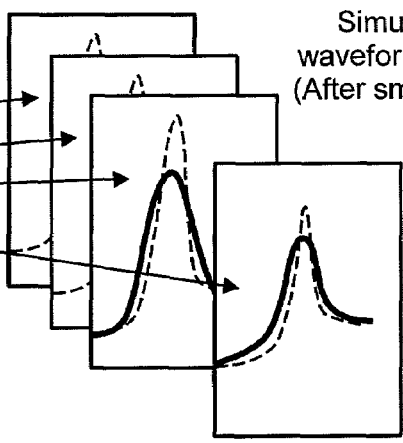

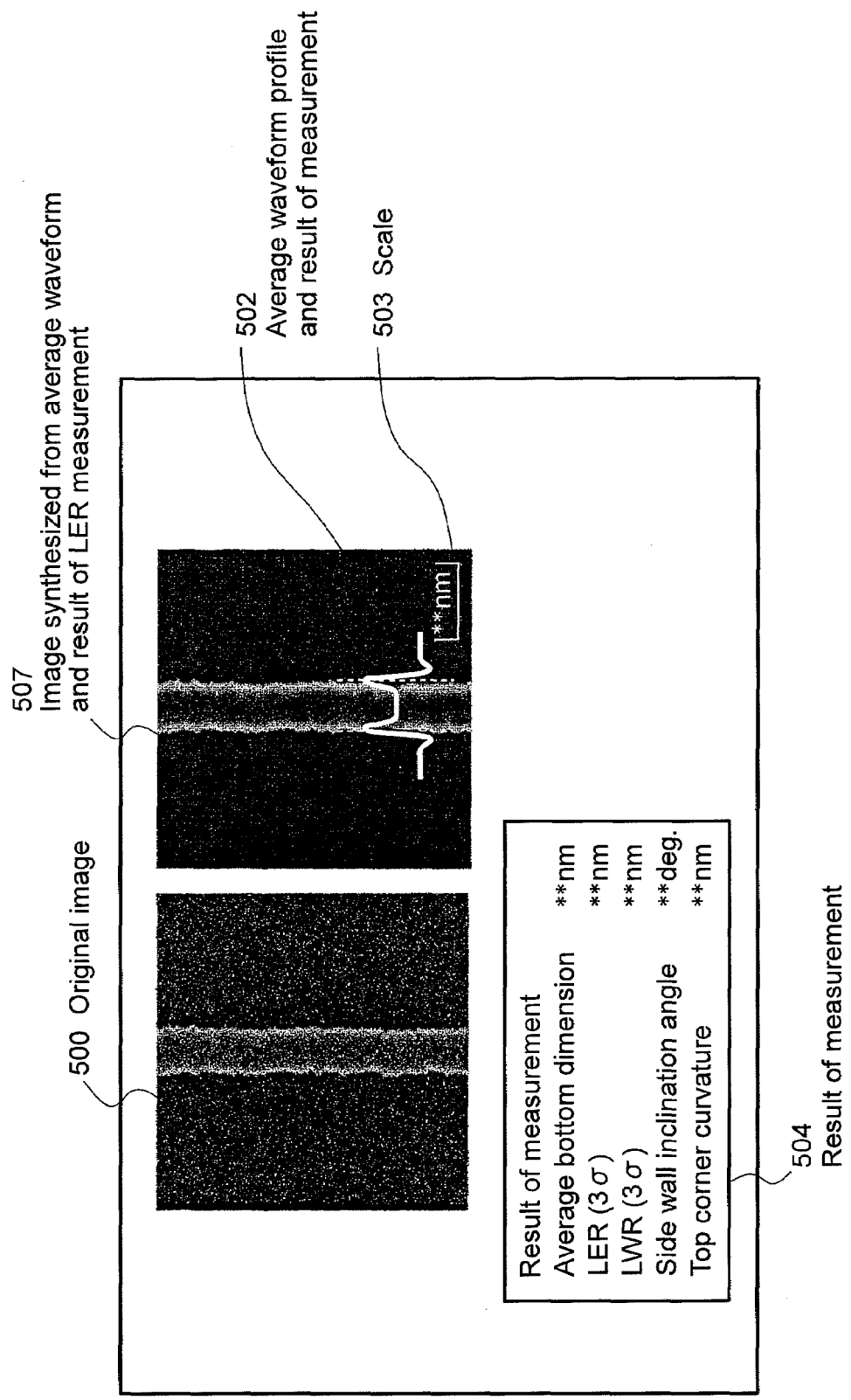

Measurement target pattern

Note: Signal waveform in the below graph is an enlargement of only a left edge.

Average waveform generating method

510 SEM image of hole pattern

511 Provisional center of hole

512 SEM image after coordinate transformation

513 Provisional center of hole after coordinate transformation

METHOD AND APPARATUS FOR MEASURING PATTERN DIMENSIONS

CLAIM OF PRIORITY

The present application claims priority from Japanese application serial no. JP2007-040190, filed on Feb. 21, 2007, the content of which is hereby incorporated by reference into this application.

BACKGROUND OF THE INVENTION

1. Field of the Invention

The present invention relates to a method and system for measuring dimensions of a shape of a circuit pattern, which is formed on a wafer, using an electron microscopic image of the circuit pattern in a process of manufacturing a semiconductor device.

2. Description of Related Art

Dimensions and shape of a multi-layered pattern formed on a wafer as a substrate are important factors having a great influence on performance of the semiconductor device in a manufacturing process of a semiconductor device. In particular, a wiring pattern including a transistor gate wiring has a strong connection with its wiring width and shape, and accordingly, it is very important to build a manufacturing process to realize a desired wiring shape.

A general pattern of a semiconductor device is produced using an exposure technique. A fine pattern is formed by forming a film such as a photosensitive organic material (also called a photoresist) on a target material, exposing and developing a desired pattern, and etching the target material using the formed photoresist pattern as a mask.

In production lines of semiconductor devices, dimensions of the photoresist pattern after the exposure and development or dimensions of the pattern after the etching are commonly measured and controlled using a CD-SEM or the like. Scanning electron microscopes for line width measurement (for example, CD-SEMs (Critical dimension Scanning Electron Microscopes)), which are capable of picking up an image of a wiring with hundred thousand magnifications or above, have been conventionally used as length-measuring tools for measuring a fine wiring width of about several tens nanometers. As disclosed in [International Technology Roadmap for Semiconductors 2005 Edition, Metrology (Http://www.itrs-.net/)], measurement by CD-SEMs requires high repeatability and reliability. For measurement with high precision using an electron microscopic image (hereinafter referred to as an SEM image), it is effective to use an image with high contrast, low noise and good quality.

In the mean time, among materials commonly used in recent semiconductor manufacturing processes, there are many materials having low electron beam radiation-resistance, such as ArF resists or Low-k materials, as disclosed in [A. Habermas, D. Hong, M. Ross, W. Livesay, "193 nm CD Shrinkage under SEM: Modeling the Mechanism" Proc. SPIE 4689, pp. 92-101 (2002): (Habermas et al.)]. When a pattern made of such materials having the low electron beam radiation-resistance is measured, it is preferable to limit the amount of radiation of electron beams to be as low as possible in order to reduce damage to the pattern. In general, in measurement for a sample having low electron beam radiation-resistance, it is difficult to use a high quality image having a high S/N ratio. For this reason, such a sample has to be subjected to an image smoothing treatment or the like to reduce an effect of noise, thereby improving repeatability of measurement.

In addition, a method of measuring dimensions of a pattern in consideration of a sectional shape of the pattern with attention paid to a relationship between the pattern shape and a waveform is disclosed in [J. S. Villarrubia, A. E. Vladar, J. R. Lowney, and M. T. Postek, "Scanning electron microscope analog of scatterometry," Proc. SPIE 4689, pp. 304-312 (2002): (Villarrubia et al. −1)]. Specifically, this disclosed method is to measure a pattern sectional shape and dimensions of the pattern with high precision based on the pattern sectional shape by calculating a relationship between the pattern sectional shape and a waveform of an SEM signal through a Monte Carlo simulation, storing the calculated relationship as a library, and selecting waveform data nearest to an actual SEM image for measurement of dimensions of the pattern.

Furthermore, an example of obtaining a CD value of bottom, top, signal peak interval and the like of an SEM image signal as an example of sites selected as image features when the image features varying depending on a pattern shape are calculated from an obtained waveform is disclosed in [Chie Shishido, Ryo Nakagaki, Maki Tanaka, Yuji Takagi, Hidetoshi Morokuma, Osamu Komuro, and Hiroyoshi Mori, "Dose and focus estimation using top-down SEM images," Proc. SPIE 5038, pp. 1071-1079 (2003): (Shishido et al)].

SUMMARY OF THE INVENTION

As described in the Background of the Invention, in the measurement using the electron microscopic image, the repeatability of measurement is secured by reducing the amount of radiation of electrons to reduce damage to the pattern and reducing an effect of reduction of an image S/N ratio by the amount of radiation of electrons using an image processing means such as smoothing. However, although the image processing means such as smoothing can reduce an effect of noise, it may degrade information of the pattern shape and dimensions of the pattern. FIGS. 4 and 5 show examples of deterioration of waveform information by a smoothing process and specifically show that an original SEM image waveform is greatly changed by the smoothing process.

In addition, as disclosed in Non-Patent Document 5, a semiconductor pattern formed using a lithography technique has been known to have variation of pattern edge positions and dimensions called as line edge roughness (LER) or line width roughness (LWR). For this reason, when an averaging process in a longitudinal direction of a line as shown in FIG. 5 is performed, a signal waveform of an SEM image is deformed by an affect of this roughness, thereby making it difficult to reduce an S/N ratio by an image process without changing waveform.

On the other hand, as disclosed in [Villarrubia et al. −1], [Shishido et al.] and [J. S. Villarrubia, A. E. Vladar and M. T. Postek, "A simulation study of repeatability and bias in the CD-SEM," Proc. SPIE 5038, pp. 138-149 (2003): (Villarrubia et al. −2)], an SEM image waveform is varied depending on a shape of a target pattern. In [Villarrubia et al. −1] and [Villarrubia et al. −2], with attention paid to a difference between shapes of the target pattern, information on a sectional shape of the target pattern to be measured is acquired, or measurement is realized with high precision in consideration of the shapes of the pattern. However, in [Villarrubia et al. −2], in the method of measuring dimensions in consideration of the sectional shape of the pattern, it is disclosed that the measurement repeatability is deteriorated when an S/N ratio of the target image to be measured is poor.

In contrast, the smoothing process is effective in improving the measurement repeatability, but since the waveform variation occurring due to the smoothing process as shown in FIG. 4 or 5 deteriorates the pattern shape information, the use of such an image can not realize measurement with high accuracy in consideration of the sectional shape of the pattern, thereby making it difficult to realize measurement with high precision to meet a need of measurement high accuracy according to pattern size shrink.

It is therefore an object of the invention to realize high accurate measurement of pattern dimensions using electron microscopic image (SEM image) by reducing an effect of noise even in an image having a low S/N ratio, without deteriorating information on shape and dimensions of an original pattern. If the information on the shape and dimensions of the pattern can be obtained even in the image having the low S/N ratio, then it is possible to realize measurement of pattern dimensions with high accuracy without electron beam damage to the pattern.

To accomplish the above object, by calculating edge position deviations due to roughness of a pattern, correcting the calculated edge position deviations for signal waveforms, and averaging the signal waveform corrected edge position deviations, an average waveform having low noise at an average position is generated without degrading waveform shape information of edges. When measurement is carried out using the average waveform, it is possible to realize highly accurate measurement.

With this configuration, it is possible to realize fast and highly accurate CD-SEM measurement without electron beam damage. For even an image having a low S/N ratio, since 3-dimensional shape information of a pattern in the image can be detected with high sensitivity, it is possible to manage or control a semiconductor manufacturing process state such as pattern shape variation based on a result of pattern measurement of the invention. In addition, measurability in an image having a low S/N ratio allows reduction of time taken to acquire an image, thereby increasing throughput of pattern dimension measurement.

These and other objects, features and advantages of the invention will be apparent from the following more particular description of preferred embodiments of the invention, as illustrated in the accompanying drawings.

BRIEF DESCRIPTION OF THE DRAWINGS

FIG. 4A is a view showing an ideal image of a SD-SEM.
FIG. 4B is a view showing a signal waveform of FIG. 4A.
FIG. 4C is a view showing a SD-SEM image.
FIG. 4D is a view showing a signal waveform of FIG. 4C.

FIG. 7A is a flow chart illustrating an off-line process to prepare an SEM waveform library in a pattern measuring method according to a second embodiment of the invention.

FIG. 7B is a flow chart illustrating the pattern measuring method according to the second embodiment of the invention.

FIG. 16 is a flow chart illustrating the pattern measuring method according to the third modification of the first embodiment of the invention.

FIG. 17A is a waveform diagram showing an SEM signal waveform in a pattern measuring method according to a modification of the second embodiment of the invention.

FIG. 17B is a waveform diagram stored in a simulation waveform library corresponding to the SEM signal waveform in the pattern measuring method according to the modification of the second embodiment of the invention.

FIG. 17C is a waveform diagram showing an SEM signal waveform subjected to a one-dimensional smoothing process in the pattern measuring method according to the modification of the second embodiment of the invention.

FIG. 17D is a waveform diagram stored in a simulation waveform library subjected to a one-dimensional smoothing process in the pattern measuring method according to the modification of the second embodiment of the invention.

FIG. 19 is a front view of a screen showing a result in the pattern measuring method according to the fourth modification of the first embodiment of the invention.

DETAILED DESCRIPTION OF PREFERRED EMBODIMENTS

Hereinafter, the best mode to carry out the invention will be described by way of preferred embodiments.

First Embodiment

First, basic electron microscopic image processing of a pattern measuring method according to a first embodiment of the invention will be described with reference to FIGS. 1 to 3.

Figure 1A:
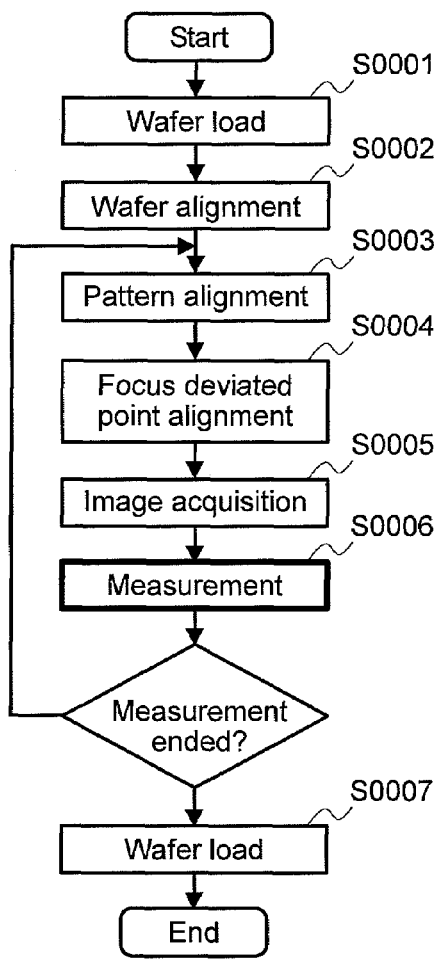
FIG. 1A is a flow chart illustrating a pattern measuring method according to a first embodiment of the invention.
Figure 1B:
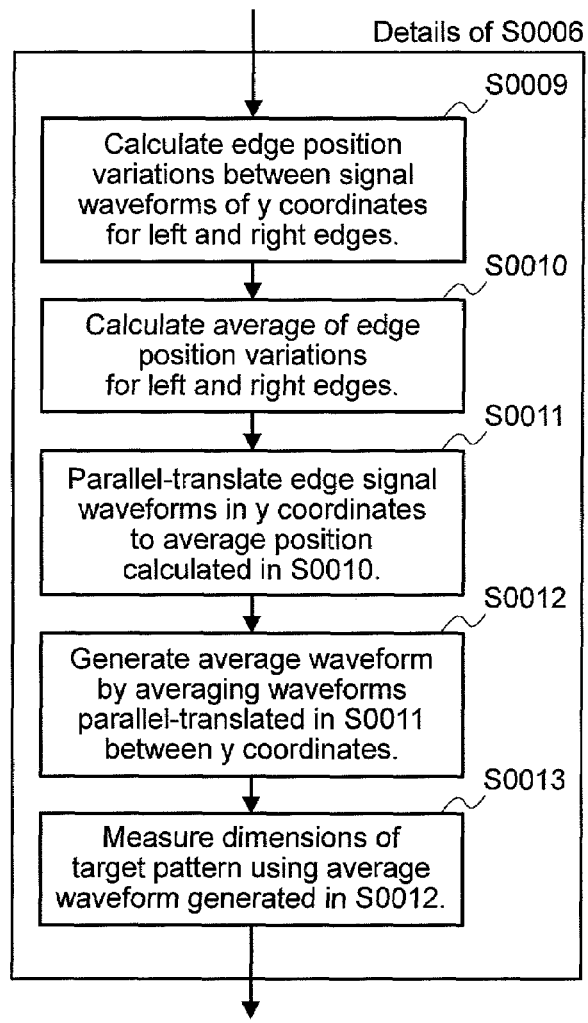
FIG. 1B is a flowchart illustrating details of Step S0006 in the flow chart of FIG. 1A.

FIG. 1A shows one example of measurement procedure using a SD-SEM in the pattern measurement method of the invention. FIG. 1B is a flow chart illustrating details of Step S0006 in the flow chart of FIG. 1A.

Actual measurement is carried out in an order shown in FIG. 1A. First, a wafer is loaded into an apparatus in a similar way in normal SD-SEM measurement (S0001), and a position of a pattern on the wafer is corrected by wafer alignment (S0002). Next, a stage is moved near the pattern to be measured, and accurate positioning using preset neighboring patterns (S0003) and image quality is adjusted by focus and astigmatism/focus adjustment (S0004). Thereafter, a SEM image of the pattern to be measured is acquired (S0005) and then measurement for the pattern is carried out (S0006).

FIG. 1A shows an example of measurement immediately after the image acquisition, but only the image may be acquired in advance and the measurement may be separately carried out. In this case, instead of Step S0006 of FIG. 1A, image recording (not shown) or image transmission (not shown) is carried out, image data are recorded in a recording medium, and the measurement may be separately carried out by image processing unit 300 in FIG. 3. In a case where a plurality of patterns are measured on the same wafer, Step S0003 to Step S0006 are repeated to measure all the patterns or acquire all the images of the patterns to be measured, as shown in FIG. 1A. Upon completing the image acquisition, the wafer is unloaded from the apparatus (S0007).

FIG. 1B explains details of Step S0006 of FIG. 1A in the image processing according to the first embodiment of the invention. After acquiring the image of the pattern to be measured, in the SEM image of the pattern to be measured, relative variation of edge positions at each Y coordinate is calculated for each of left and right edges (S0009). Next, an average of the variation of edge positions calculated in Step S0009 is calculated for each of left and right edges (S0010). Next, an SEM image signal waveform in each Y coordinate is shifted in X direction to the average edge position calculated in Step S0010 to produce a waveform moved to the average edge position calculated in Step S0010 (S0011). Next, the produced waveforms in different Y position shifted to the average edge position are averaged with waveforms in a Y direction to produce an average waveform (which will be in detail described later) (S0012).

Next, the average waveform obtained so is subjected to an edge position detecting process to calculate edge positions of left and right patterns of the average waveform in the acquired SEM image. Then, an average dimension of the pattern to be measured is calculate based on a difference between the calculated edge positions (S0013).

As disclosed in [Yamaguchi et al.], the edge positions of the pattern may be varied by several nanometers or so due to LER even in a relatively narrow range. In this connection, from review by the inventors, in a general semiconductor manufacturing process, it can be known that shape variation of a pattern side wall in the same edge of the same pattern is relatively small compare to the variation of edge positions. If the shape variation of the pattern side wall is small like this, when the variation of the edge positions is considered in advance with the order shown in FIG. 1B, it is possible to attain an effect of noise reduction by an averaging process and carry out stable measurement with sufficiently small shape variation of a waveform and without having an effect on an SEM waveform.

Figure 2A:
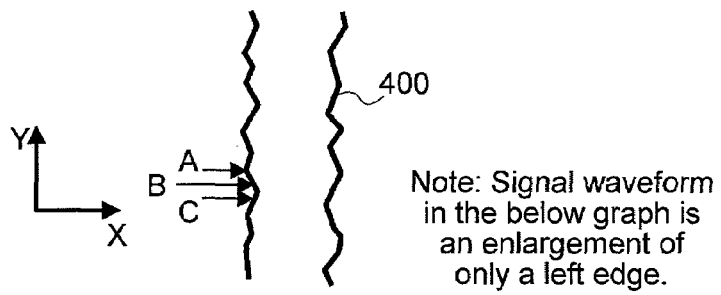
FIG. 2A is a plan view of a line pattern as an object to be measured.
Figure 2B:
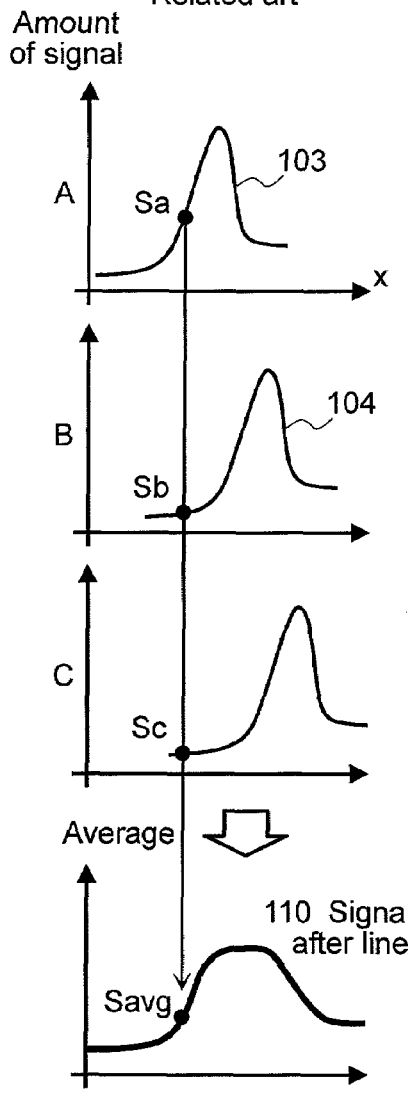
FIG. 2B is a graph showing a conventional line addition signal waveform.

FIG. 2 shows the concept of the procedure shown in FIG. 1. FIG. 2A is a top-down view of a line pattern 400 as an object to be measured. A SD-SEM typically carries out measurement using a two-dimensional image taken from the same direction as FIG. 2A. As shown in FIG. 2, a line pattern dimension has a deviation, and positions of edges of the line pattern (line edge roughness (LER)) and dimensions of edges of the line pattern (line width roughness (LWR)) are varied by a y coordinate. Accordingly, as shown in FIG. 2, waveforms of edges in different y coordinates (A, B and C) becomes waveforms as shifted in an x direction according to variation of the edge positions (in actuality, shape of the waveforms is also varied due to a subtle difference between object sidewall shapes, and noises). The related art of FIG. 2B attempts to reduce noises by averaging the amount of signal between waveforms in the same x coordinate without considering this roughness.

FIG. 2B shows the related art. As shown in FIG. 2B, since the positions of edge are different from each other in the coordinates A, B and C, positions of peaks of signal waveforms are also varied. For example, a signal waveform 103 in the y coordinate A is different in position in the x direction from a signal waveform 104 in the y coordinate B although they have the same shape. For such signal waveforms, the related art reduces noises by an averaging effect that an average value Savg is calculated by averaging the amount of signals Sa, Sb and Sc of the same x coordinate of the y coordinates A, B and C, for example, and likely, an average value is calculated for all x coordinates (hereinafter, this process is called simple scan line addition or averaging). As shown in FIG. 2B, averaged waveform 110 has different shape from the original waveforms 103 and 104. In contrast, in the pattern measuring method of the invention shown in FIG. 1B, deviation of positions in the x direction between images of y coordinates is calculated in advance as shown as arrows in FIG. 2C, and an averaging (line addition) process is carried out after correcting the deviation and combining corrected positions in the x direction, as shown in FIG. 2C.

Figure 2C:
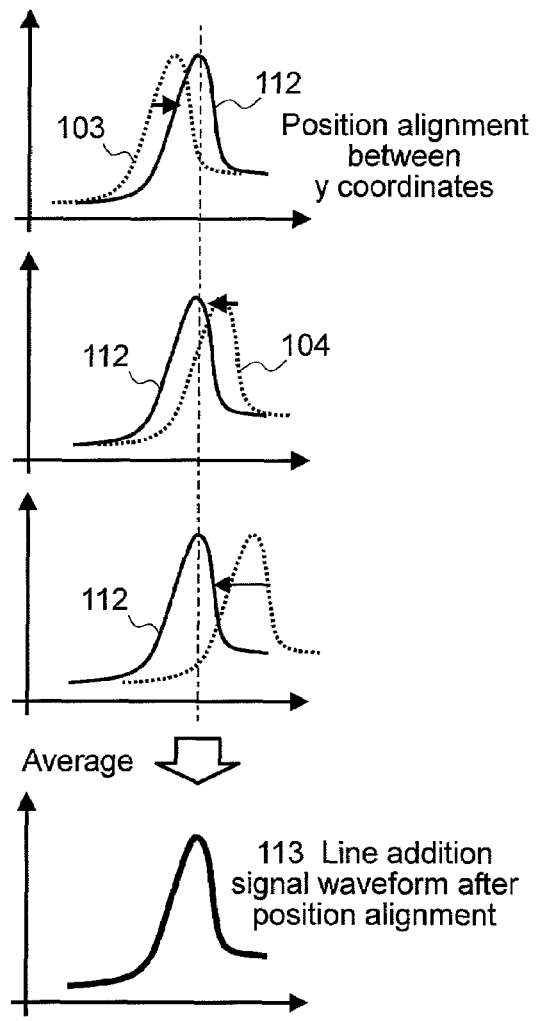
FIG. 2C is a graph showing a line addition signal waveform in the pattern measuring method according to the first embodiment of the invention.

A reference numeral 112 shown in FIG. 2C denotes a signal waveform after alignment to move an original signal waveform 103 and 104 in the x direction based on calculated deviation of edge positions (in actuality, since the waveforms 103 and 104 are different from each other due to noises or a subtle difference in sectional shape between patterns, the waveforms of the coordinates A, B and C do not become identical with each other even by the position alignment). When the position aligning process of the invention is carried out, it is possible to suppress deterioration of information on the shape of the target pattern included in the original waveform. Since a scan line addition (or averaging) after the position alignment of FIG. 2C is subjected to an averaging process according to an average value of position deviations, a generated waveform having an average shape for each edge can be disposed at an average position. In the specification, this waveform having the average shape is called an average waveform (see Step S0012).

The position deviation in the x direction may be calculated using a general position deviation calculating method. For example, with a selected reference waveform as a template, correlation between a target waveform in a y coordinate and the template may be calculated with positions in an x direction deviated, and a site having highest correlation may be selected. If an S/N ratio of an image is very low, it is difficult to obtain a reliable result in calculating the position deviation. So, after completing Step S0012 in the flow chart of FIG. 1B, with the average waveform calculated in Step S0012 as a template, when edge position variation is calculated again and Steps S0009 to S0012 are repeated (not shown), it is possible to improve precision of detection of the position deviation and hence carry out more stable measurement. Other methods to realize highly reliable position alignment for an image having a very low S/N ratio will be described in first to fourth modifications of the first embodiment.

Figure 3:
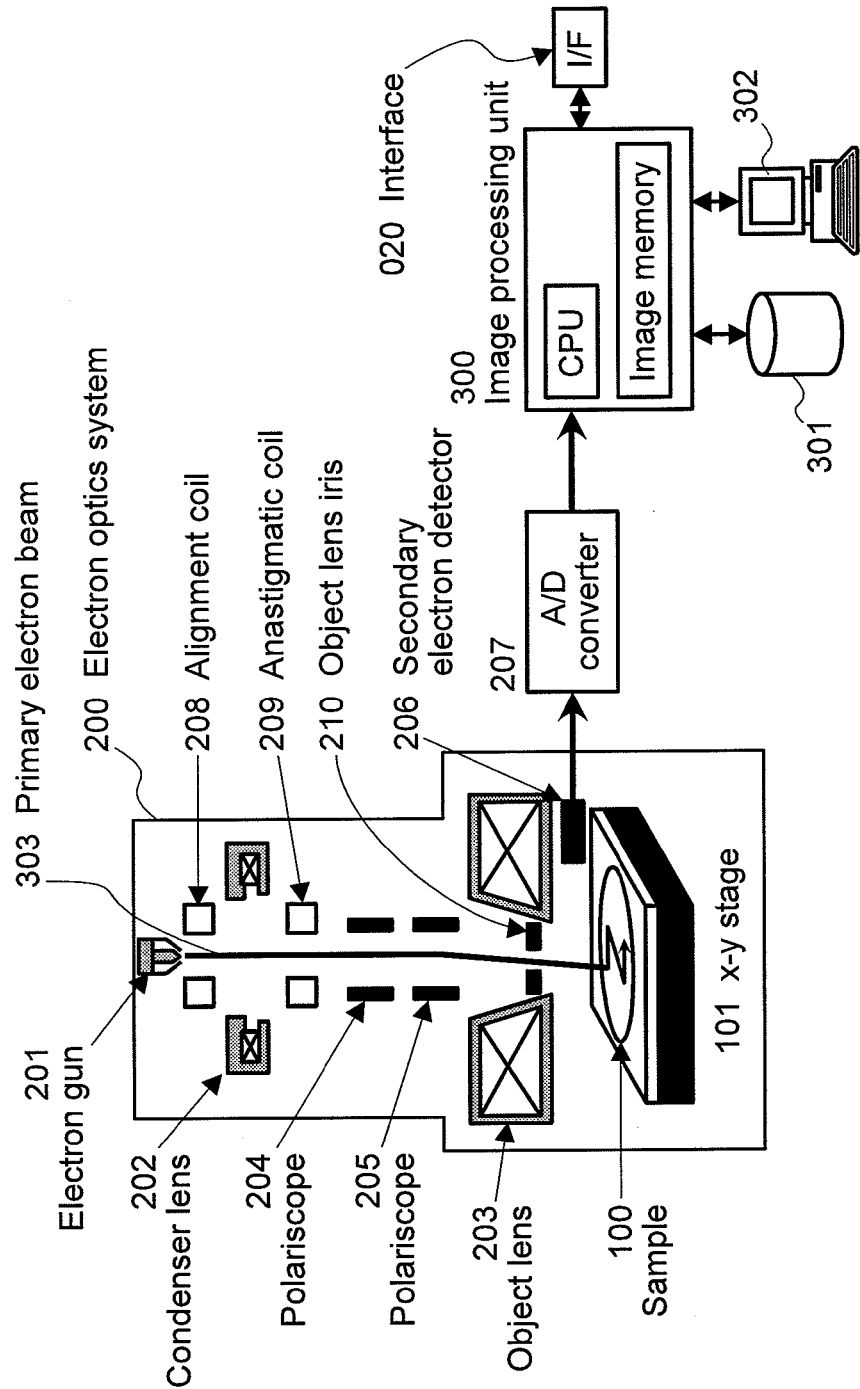
FIG. 3 is a block diagram showing a system configuration of a SD-SEM to perform the pattern measuring method of the invention.

FIG. 3 shows a system configuration of a general CD-SEM used to acquire an image. In an electron optics system 200, a primary electron beam 303 emitted from an electron gun 201 is focused by an alignment coil 208, a condenser lens 202, an anastigmatic coil 209, an object lens 203 and an object lens iris 210 and a sample 100 is irradiated with the focused electron beam. When the sample 100 is irradiated with the electron beam, secondary electrons or reflected electrons are generated from an irradiated portion of the sample 100 depending on material or shape of the sample 100. The secondary electrons generated by two-dimensionally scanning with the primary electron beam 303 using polariscopes 204 and 205 are detected and converted to an electrical signal by a secondary electron detector 206, and then the electrical signal is converted to a digital signal by an A/D converter 207, thereby obtaining a secondary electron beam image as a two-dimensional digital image. In general, a secondary electron beam image is used for dimension measurement in a semiconductor process. Hereinafter, an electron beam image or an SEM image refers to the secondary electron beam image.

The obtained image is stored in a storage medium 301 and is processed by an image processing unit 300. Alternatively, the image may be transmitted to an external image processing unit (not shown) for processing of the image, after being once stored in an external image database (not shown), or directly via an external interface 020. Operations and results of the system are displayed on a display device 302.

Next, the problem to be solved by the invention and the image processing of the invention will be described in detail with reference to FIGS. 4A to 4D. Images and waveforms shown in FIGS. 4A to 4D are generated through a simulation, and the images are SEM images having a long wiring pattern in a vertical direction (y direction). FIGS. 4A and 4C show an example of SEM images having the line pattern 400 having a length on a flat underlying portion 401.

As shown in FIGS. 4A and 4C, in the wiring pattern, since an edge portion of the line pattern 400 is brighter than other flat portions (the underlying portion 401, and upper portions of the pattern, that is, a portion between two peaks of signal waveforms), a position of the pattern edge is detected by an image processing using variation of the amount of signal. FIG. 4A shows an ideal CD-SEM image 100 without any noise and roughness. FIG. 4C shows a measurement target image obtained through a simulation using an actual CD-SEM, specifically, a CD-SEM image 102 having roughness (LER and LWR) in a pattern. Signal waveforms 103 and 104 of FIG. 4D corresponding to the image of FIG. 4C are equal to a signal waveform 101 of FIG. 4B corresponding to the image of FIG. 4A, but it can be seen from FIG. 4D that image signals are deteriorated by noises with their waveforms 103 and 104 changed greatly.

In order to reduce noises of the SEM image, it is effective to increase the amount of beam current of the primary electron beam irradiating and scanning the sample when the SEM image is acquired, increase irradiation time per area of the sample by decreasing a scanning speed of the primary electron beam, or increase the number of addition frames (a process of totaling image signals for a plurality of frames obtained by obtaining an image of one frame several times by irradiation and scan of an electron beam focused on a particular region) However, in a case where an SEM image of a material having low resistance to electron beam irradiation is acquired, it is difficult to use such methods. Such method may be applied to process images having lots of noises.

Noises shown in FIG. 4C are produced since the amount of irradiation of electron beam is decreased to reduce damage to a pattern by the electron beam irradiation, and the noises are likely to occur in an actual CD-SEM. In addition, in FIG. 4D, since noises when the image is acquired are randomly varied in addition to variation of the position of the peak by roughness, the CD-SEM signal waveforms 103 and 104 become completely different although shapes of their original peak portions are identical.

In the conventional pattern dimension measuring method, for example, as shown in the signal waveform of FIG. 4B, with the amount of signal of a waveform peak corresponding to a pattern edge and the amount of signal of an underlying portion as a reference, a point having a specified percentage of a difference therebetween (50% in case of the FIG. 4B) is assumed to be an edge position, left and right edge positions are calculated, and pattern dimensions are measured based on the difference (hereinafter referred to as a threshold).

However, as shown in FIG. 4D, since the amount of irradiation of electron beam for a pattern made of a material prone to damage is reduced, a signal waveform may be deteriorated by noises, thereby making it difficult to carry out stable measurement with the threshold or the like. In contrast, the conventional measuring method realizes stable measurement by removing noises occurring due to the image processing.

Figure 5:
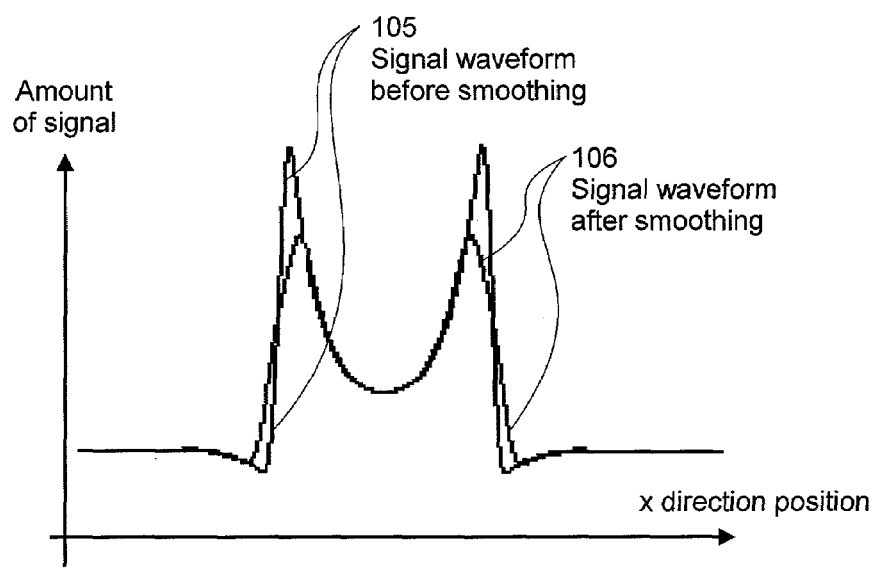
FIG. 5 is a signal waveform diagram showing SEM signal waveforms before and after a smoothing process in no consideration of edge roughness.

FIGS. 5 and 6 show an example of a noise removing process of the conventional CD-SEM measurement and a problem in the measurement. FIG. 5 shows an example of a smoothing filter process. As can be seen from FIG. 5, from the fact that a signal waveform 105 before being smoothed becomes different in shape and amount of signal of edge portion from a smoothed signal waveform 106, although an edge position detecting process is performed with the same method, a detected edge position may be varied before and after the smoothing process. Although a simulation image with no noise is illustrated to clarify an effect of waveform variation, noises may be actually included in the signal waveform, as shown in FIG. 4B. Although the effect of noises can be reduced and the measurement can become stable by removing a high frequency component by the smoothing process, a measurement value may be varied before and after the smoothing process, as described above.

Figure 6A:
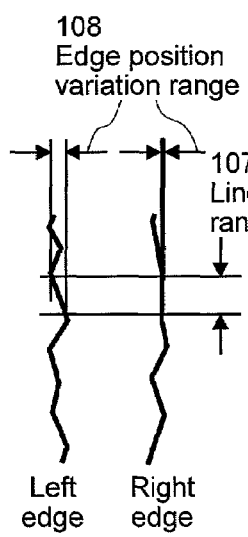
FIG. 6A is a signal waveform diagram showing an SEM signal waveform before a smoothing process in consideration of edge roughness.
Figure 6B:
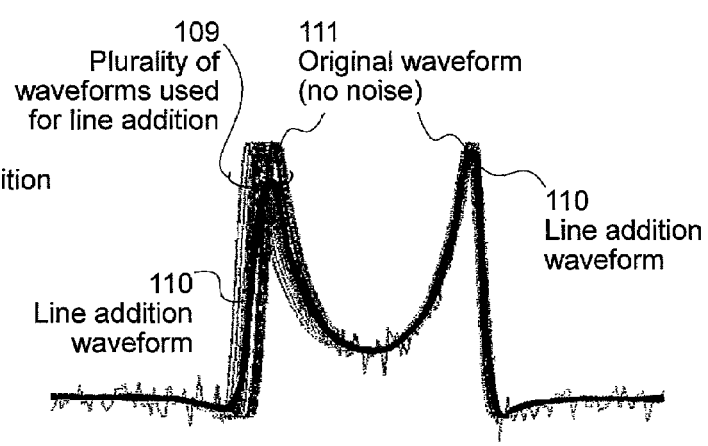
FIG. 6B is a signal waveform diagram showing an SEM signal waveform after a smoothing process in consideration of edge roughness.

FIG. 6 shows a process called as line addition in the related art shown in FIG. 2, specifically, a method of removing noises by averaging image signals at different positions in a y direction using the fact that a wiring pattern image lies in parallel to the y direction. Although effective in removing noises if the target pattern has no roughness like the image shown in FIG. 4A, this method may not obtain a correct result if the target pattern has any roughness as shown in FIG. 4B. FIG. 6 shows an example of averaging a plurality of signal waveforms 109 as shown in FIG. 6B in a certain y coordinate range 107. In an example shown in a schematic view of FIG. 6A, ranges of variation 108 of left and right edge positions in a waveform average range are different from each other. Since the right edge has low edge variation, shape of an original waveform is little varied even by averaging the plurality of waveforms.

On the other hand, in the left edge, since waveforms having large position deviation are averaged, a waveform 110 obtained by the line addition is greatly varied from a signal waveform 111 before the line addition, as shown in FIG. 6B. Accordingly, when the line addition process is formed like the example of the smoothing process shown in FIG. 5, a measurement value before the line addition may be varied from a measurement value after the line addition. In addition, in the example of the smoothing process shown in FIG. 5, when the two-dimensional filter process is performed, since a result of the smoothing is varied due to roughness of an edge portion, an effect of a filer by a site becomes unstable.

In contrast, the average waveform generating process of the invention can reduce noise with side wall shape information of a target pattern kept unchangeable. For example, when SEM image data corresponding to 100 pixels in a y direction are used, noises can be reduced to a reciprocal of a square root of the number of pixels, that is, about a tenth. For example, if n data are randomly extracted from a population obeying a normal distribution, according to a statistical effect, a distribution of an average value of n data becomes a normal distribution having a standard deviation obtained by removing a standard deviation of the population from a square root of n. In this manner, noises in the amount of signal of the SEM image are random, and, as the number of pixels used for the averaging process increases, noises can be further reduced accordingly.

Although the first embodiment shows the example of calculating the average waveform using waveforms at different y coordinates in one image, the number of images is not necessarily one, but it should be understood that more images obtained by dividing and picking up an image on the same edge of a sample into two or more may be used. In this case, since the amount of used signal increases, it is possible to obtain a higher noise reduction effect.

As shown in FIGS. 5 and 6, since the noise removing process of the related art varies an original signal waveform, sensitivity to variation of pattern shape or dimensions may be lowered although a measurement result may stable. In particular, since a peak shape of an edge waveform is spread in a horizontal direction, a measurement result becomes larger than actual dimensions.

In contrast, when the average waveform is generated according to the invention shown in FIG. 1, and pattern dimensions are measured or information of a pattern cubic shape is estimated using the generated average waveform, it is possible to solve the problem occurred in the conventional smoothing process. That is, since the average waveform generating process of the invention considering any roughness of a sample not only reduces noise but also calculates a waveform at an average position in an image to be processed with a signal waveform of an edge kept unchangeable, it is possible to reduce a dimension variation component, which is not derived from an original pattern but may occur when the smoothing process is performed similar to the related art, and carry out measurement safely with high precision and high sensitivity. Accordingly, although an SEM image having a low S/N ratio is used for a material having low resistance to electron beam irradiation, it is possible to realize stable measurement with relatively low amount of electron irradiation, that is, with less damage.

Although FIG. 3 shows the system using the secondary electron image of SEM, the system may use reflected electrons. Alternatively, the system may use FIB using light ions instead of an electron beam. Using the FIB, since a scattering angle in a solid is relatively small, it is possible to carry out measurement with high resolution power.

First Modification of First Embodiment

Although the pattern dimension measurement can be carried out with high precision and high sensitivity by generating the average waveform considering roughness of the target pattern, as shown in the first embodiment, in some cases where an S/N ratio of an image is very low, measurement for position deviation may not be carried out well due to roughness. In a first modification of the first embodiment, a method of performing a position aligning process with high precision will be described with reference to FIG. 12.

Figure 12A:
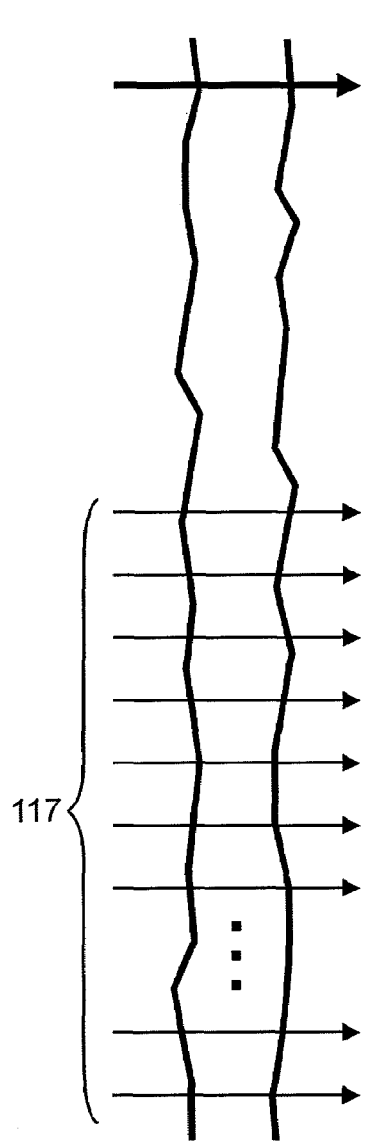
FIG. 12A is a schematic plan view showing a line pattern.
Figure 12B:
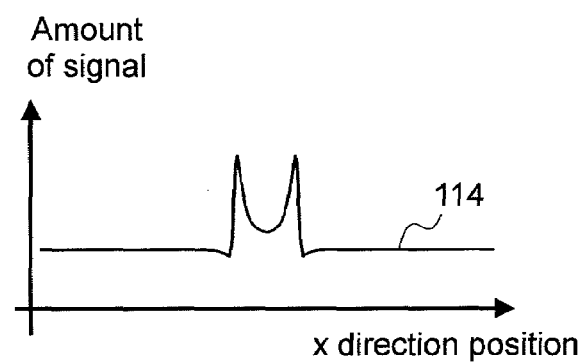
FIG. 12B is a signal waveform diagram showing an SEM signal waveform prepared as a template having a high S/N ratio, which is obtained through a plurality of scans and an addition, according to a first modification of the first embodiment of the invention.
Figure 12C:
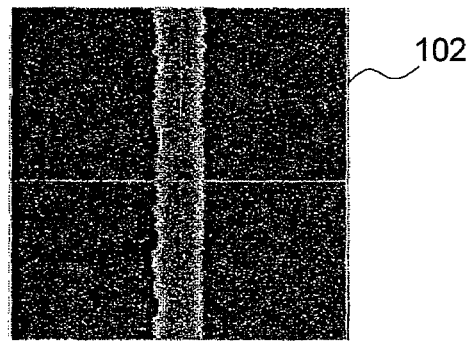
FIG. 12C is a view showing a normal SEM image and FIG. 12D shows its SEM signal waveform.
Figure 12D:
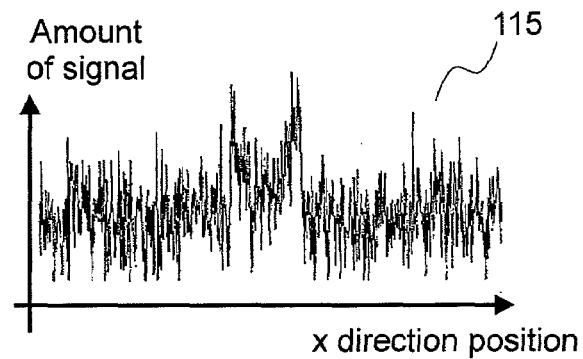

In the first modification, when position deviation between signal waveforms of edge portions is calculated, the precision of detection of the position deviation can be enhanced by using a template with a high S/N ratio. FIG. 12A is a schematic view showing a relationship between a measurement target pattern and an electron beam scan position. FIG. 12C shows an SEM image 102 obtained by scanning an electron beam scan position 117 of normal SEM image acquisition, and FIG. 12D shows a signal waveform 115 of an SEM image 102. Typically, as shown in FIG. 12C, a two-dimensional image signal is obtained by scanning an electron beam with certain intervals in a y direction. The number of scans in each y coordinate is not limited to one, but an average of a plurality of scans is commonly used. As described above, in the sample having low resistance to the electron beam irradiation, since the amount of electron beam irradiation (adjusted by the amount of current, the number of scans, a scan speed or the like) is reduced to be as low as possible, an S/N ratio of the signal waveform 115 becomes very low, as shown in FIG. 12D.

Accordingly, in the first modification, in order to estimate the amount of shift of an edge position in a normal image, sites other the measurement position are irradiated with more electrons than normal to thereby acquire a signal waveform having a relatively highs/N ratio and use the acquired signal waveform as a template. For example, as shown in FIG. 12B, when an average waveform is obtained by scanning the same site by more times than normal, the signal waveform 114 obtained by multiplication of the plurality of scans has an S/N ratio higher than that of the signal waveform 115 obtained by a normal scan. Although the more amount of electron beam irradiation gives more damage, if the amount of electron beam irradiation is limited to a very narrow range, an effect of the damage is sufficiently suppressed to be small as compared to electron beam irradiation in a two-dimensional wide range. Accordingly, as shown in FIG. 12, an average signal waveform may be generated by scanning as more as possible on the same edge as a measurement target region at sites remote in the y direction in a range having no damage problem.

In this manner, when one signal waveform having an S/N ratio higher than the normal scan is obtained, using a correlation value between an edge waveform, as a template, obtained from data on the signal waveform and a measurement target waveform when an x coordinate is excluded, left and right edge position deviation of y coordinates of a measurement target image may be produced. In this manner, using the template having the high S/N ratio, it is possible to detect more stable position deviation than that of the signal waveform 115 having the low S/N ratio.

Although FIG. 12A shows the electron beam scan direction from left to right for convenience' sake, the electron beam scan direction is not particularly limited. In particular, for a normal image, the scan direction may be optional as long as the same two-dimensional image can be obtained. In addition, a relationship between a multi-scan signal waveform acquisition position and a normal measurement position is not particularly limited to FIG. 12 as long as the relationship falls within a range of a pattern formed on the same edge with the same conditions (ambient pattern density or the like).

By using the first modification, since the average waveform generating process of the first embodiment can be performed with higher precision, it is possible to obtain a higher effect of the first embodiment and realize more stable dimension measurement with high precision, estimation of a cubic shape, estimation of process variation using the cubic shape, etc.

Second Modification of First Embodiment

In a second modification, like the first modification, another method of performing an edge position aligning process with high precision in consideration of roughness will be described with reference to FIGS. 13 and 14.

In the second modification, when position deviations between signal waveforms of edge portions are calculated, a signal waveform having a high S/N ratio is separately generated as a template for position alignment. In the second modification of the first embodiment shown in FIG. 14, a line addition process is performed in advance within a range having no effect on a waveform shape. FIG. 13 shows a frequency characteristic of general semiconductor line pattern wiring width deviation as disclosed in Non-Patent Document 6. As can be seen from FIG. 13, the wiring width deviation has a relatively large amplitude in a low frequency domain while having a suddenly decreasing amplitude in a high frequency domain. This locates at a relatively near site since an edge of a wiring at a distance corresponding to a frequency of a range in which the amplitude of the wiring width deviation becomes sufficiently small is more affected by a low frequency. That is, it can be said that the wiring width is not suddenly varied.

Figure 13:
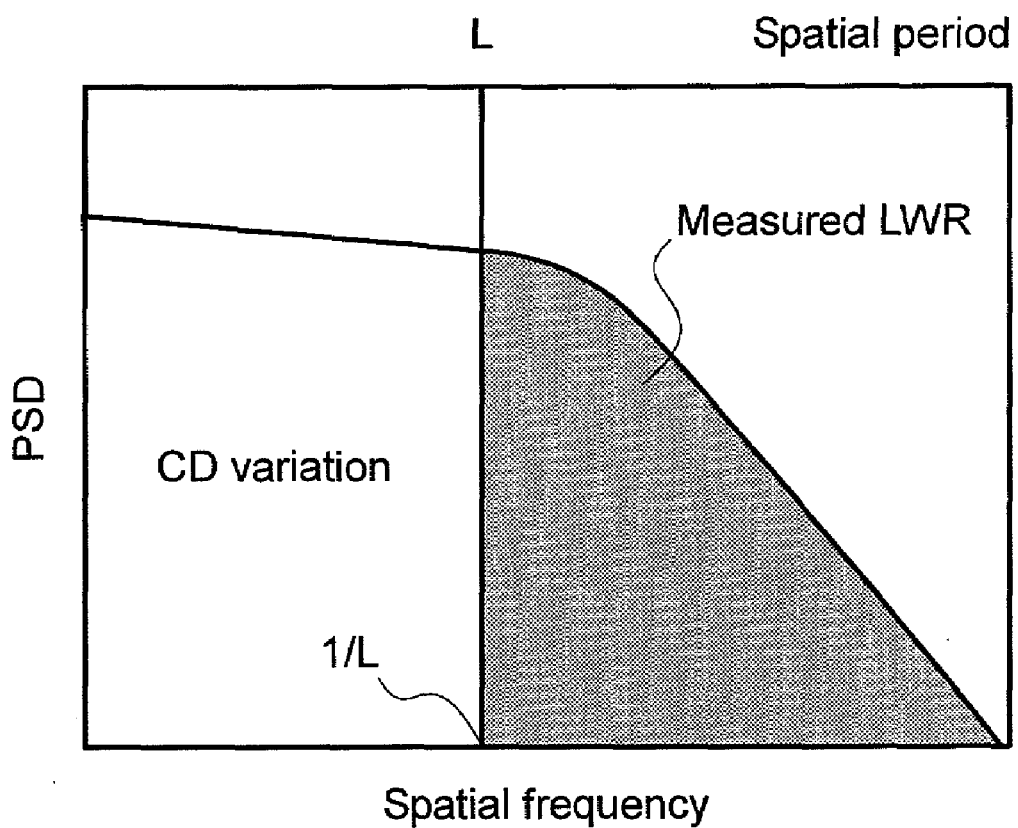
FIG. 13 is a view illustrating a general characteristic of line width roughness of a semiconductor pattern disclosed in [Yamaguchi et al].

Using this phenomenon, although the line addition process shown in FIG. 6 is performed for waveforms of edges at a distance sufficiently closer than a distance corresponding to L shown in FIG. 13, it is possible to suppress an effect on a waveform shape to be sufficiently small. General values of L shown in FIG. 13 are disclosed in [Atsuko Yamaguchi, Hiroshi Fukuda, Hiroki Kawada, and Takashi Iizumi, "Impact of Long-Period Line-Edge Roughness (LER) on Accuracy in CD Measurement," Proc. SPIE 5752, pp. 1362-1370 (2005): (Yamaguchi et al.)]. Since frequency L=3(1/μm), that is, a wavelength is 333 nm, when a signal waveform is sampled with a pitch of 333/m nm or less (where, m is an integer), edge position variation between waveforms to be added is sufficiently small, and accordingly, information of edge positions and edge waveform shapes can be maintained even with the m number of addition processes.

Figure 14:
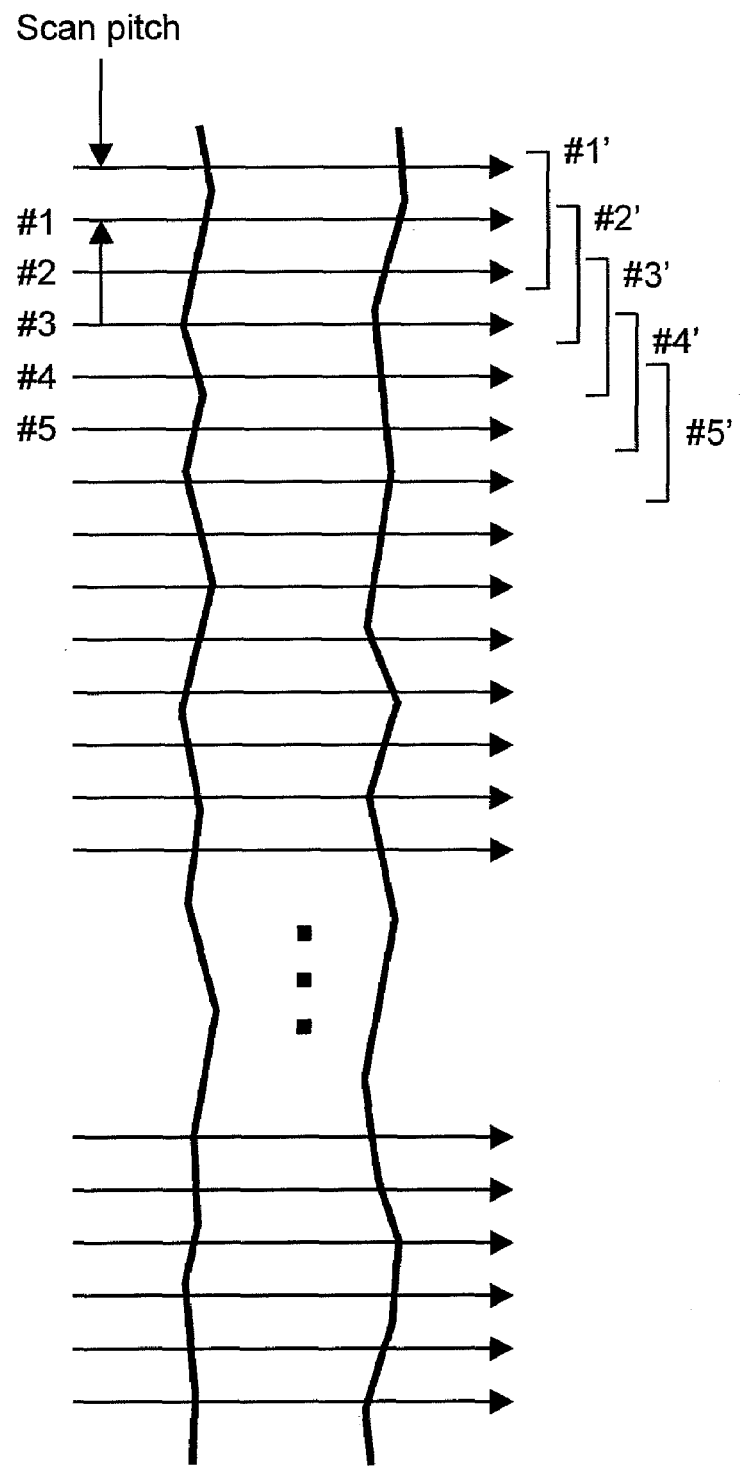
FIG. 14 is a schematic plan view of a line pattern showing a line scan pitch in a pattern measuring method according to a second modification of the first embodiment of the invention.

Accordingly, as shown in FIG. 14, by performing in advance the line addition process with the obtained m signal waveforms (m=3 in FIG. 14), it is possible to enhance an S/N ratio of a signal waveform without increasing the amount of electron beam irradiation, and hence improve the precision of position alignment for the average waveform generation described in the first embodiment.

Although FIG. 14 shows the electron beam scan direction from left to right for convenience' sake, the electron beam scan direction is not particularly limited. In particular, for a normal image, the scan direction may be optional as long as the same two-dimensional image can be obtained. In addition, a relationship between a multi-scan signal waveform acquisition position and a normal measurement position is not particularly limited to FIG. 14 as long as the relationship falls within a range of a pattern formed on the same edge with the same conditions (ambient pattern density or the like).

By using the second modification, since the average waveform generating process of the first embodiment can be performed with higher precision, it is possible to obtain a higher effect of the first embodiment and realize more stable dimension measurement with high precision, estimation of a cubic shape, estimation of process variation using the cubic shape, etc.

Third Modification of First Embodiment

In a third modification, like the first and second modifications, another method of performing an edge position aligning process with high precision in consideration of roughness will be described with reference to FIGS. 15 and 16.

Figure 15:
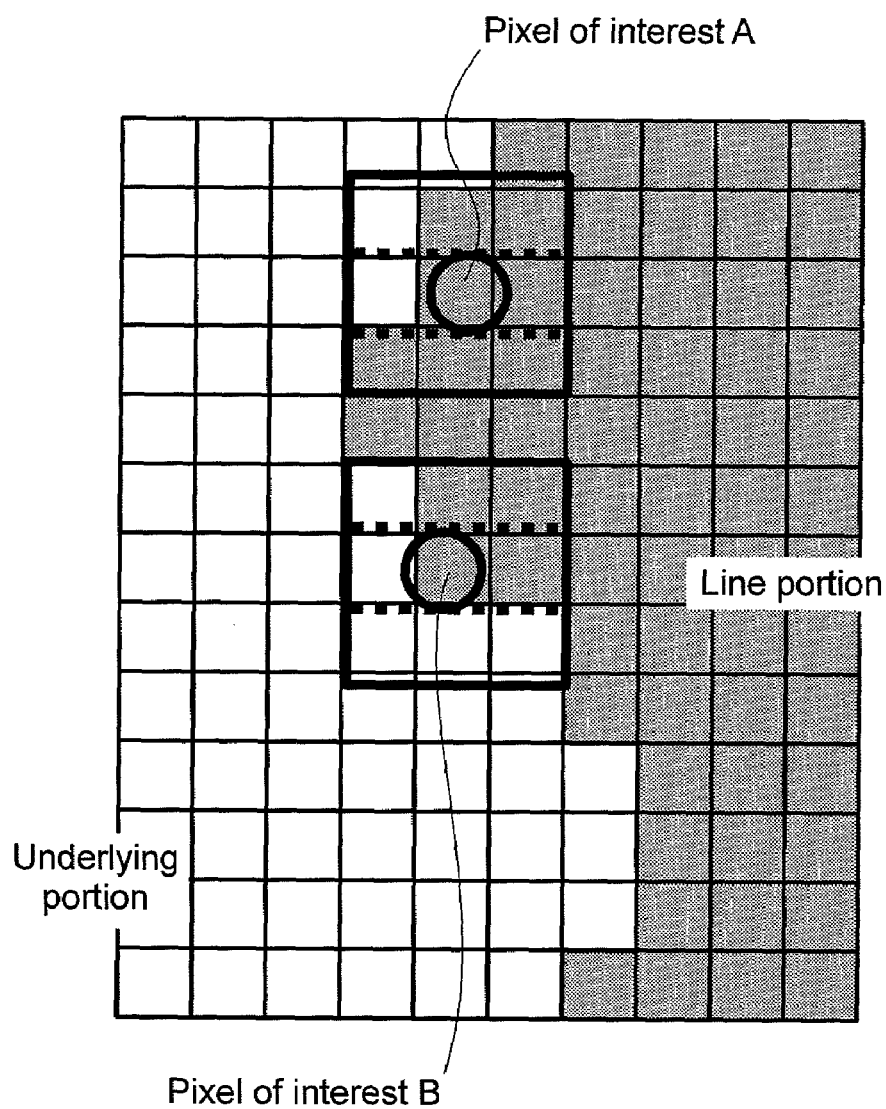
FIG. 15 is a view illustrating a one-dimensional smoothing process in a pattern measuring method according to a third modification of the first embodiment of the invention, showing an image including an edge of a pattern schematically shown to know a relationship between an edge position in a pattern edge portion and pixels of the image.

In the third modification of the first embodiment as shown in FIGS. 15 and 16, an affect of noises is reduced by applying a smoothing filter before calculating edge position deviation. Since the image smoothing process deforms a signal waveform, as shown in FIG. 5, this smoothing process requires special care in application to an image to be measured, however, if the same smoothing process is applied to both of waveforms whose position deviations are compared to each other, there occurs no particular problem.

FIG. 15 shows a relationship between an edge position in a pattern edge portion and pixels of the image. A right gray portion denotes a line pattern (line portion) and a left white portion denotes an underlying portion. Two pixels A and B of interest shown in FIG. 15 correspond to the pattern edge portion, but have different relationships with neighboring edge positions.

For example, when a smoothing filter of 3×3 pixels is applied to an image acquired with such a positional relationship, neighboring 9 pixels of the pixel A include more of the line portion while neighboring 9 pixels of the pixel B include more of the underlying portion. Accordingly, after performing the image smoothing process, the edge positions in the image are shifted in such a manner that a line of the pixel A becomes thicker than an actual line while a line of the pixel B becomes thinner than an actual line. Accordingly, when the prior two-dimensional smoothing process is performed, it is difficult to calculate correct edge position deviation between the pixels A and B which have to have the same edge position.

In the third modification, as indicated by dotted lines in FIG. 15, the smoothing process is performed using only the pixels of interest and an image signal of the same y coordinate. Then, since the same filter is applied to the same signal waveform for both of the pixels A and B, calculation of edge position deviation is not affected although a shape of an original waveform may be varied.

In the third modification, accordingly, as shown in FIG. 16, the edge position variation is calculated using an SEM signal waveform of each y coordinate with noises removed by applying a one-dimensional smoothing filter, not using the signal waveform of the original image. FIG. 16 explains a process order other than the process order explained in FIG. 1A, specifically a process order corresponding to Step S0006 in FIG. 1A for measuring the pattern dimensions from the image acquired in Step S0005 in FIG. 1A. To clarify a difference with the process order explained in FIG. 1, FIG. 16 shows combination of the process order corresponding to FIG. 1A and the data flow corresponding to FIG. 1B.

The third modification has the greatest difference with the first embodiment in that Step S1601 for applying one-dimensional smoothing filters to signal waveforms of y coordinates is added before Step S1602 for calculating edge position variation for the SEM image acquired in Step S0005.

That is, after removing noises by applying the one-dimensional smoothing filters to the signal waveforms of y coordinates in Step S1601, edge position variations are calculated using the signal waveforms with noises removed in Step S1602, an average of the calculated edge position variations is calculated (S1603), the signal waveform of the original image acquired in Step S0005, not the signal waveforms smoothed in Step S1601, is parallel-translated using variation from an average position of edge portions in the signal waveforms in the y coordinates (S1604), and an average waveform is generated by averaging the signal waveforms (S1605).

With this process of the third modification, it is possible to calculate the average waveform at the average position without deteriorating a signal waveform used for pattern dimension measurement and shape information extraction. Pattern dimension measurement is carried out using the average waveform obtained so (S1606).

In this manner, by calculating the edge position variation using the SEM signal waveforms of the y coordinates with noises removed by applying the one-dimensional smoothing filters, it is possible to generate the average waveform stably with higher precision than the first embodiment. Further, by using the third modification, it is possible to obtain a higher effect of the first embodiment and realize more stable dimension measurement with high precision, estimation of a cubic shape, estimation of process variation using the cubic shape, etc. Although FIG. 16 shows the method of making the first embodiment more precise, this method may be used for dimension measurement and cubic shape estimation in consideration of a cubic shape, which will be described later as a second embodiment, or semiconductor manufacturing process estimation using image features, which will be described later as a third embodiment, instead of the dimension measurement in S1606.

It will be appreciated that the first to third modifications may be used either separately or in combination. For combination of the first and third modifications, it is important to apply the same one-dimensional filter as that for the measurement target image to a waveform as a template.

In addition, by applying the third modification to the position aligning process explained in the first embodiment, it is possible to enhance an S/N ratio of a signal waveform used for position deviation detection without increasing the amount of electron beam irradiation, and hence improve the precision of position alignment for the average waveform generation described in the first embodiment.

Fourth Modification of First Embodiment

LER/LWR Measurement Using the Average Waveform after Position Alignment+GUI

Next, as a fourth modification, a method of applying the pattern dimension measurement explained in the first embodiment and estimating variation of dimensions and edge positions of y coordinates as well as an average dimension with high precision will be described with reference to FIG. 18.

As shown in the first embodiment, the calculated average waveform is obtained with the waveform information of the pattern edge kept unchangeable and with the edge waveform at the average position of the SEM image used for processing with low noises. Accordingly, with the edge waveform of the obtained average waveform as a template, when edge position deviation of y coordinates in the original image is calculated (S1826) and LER or LWR measurement using the calculated edge position deviation is carried out (S1827), it is possible to measure LER or LWR stably.

Figure 18:
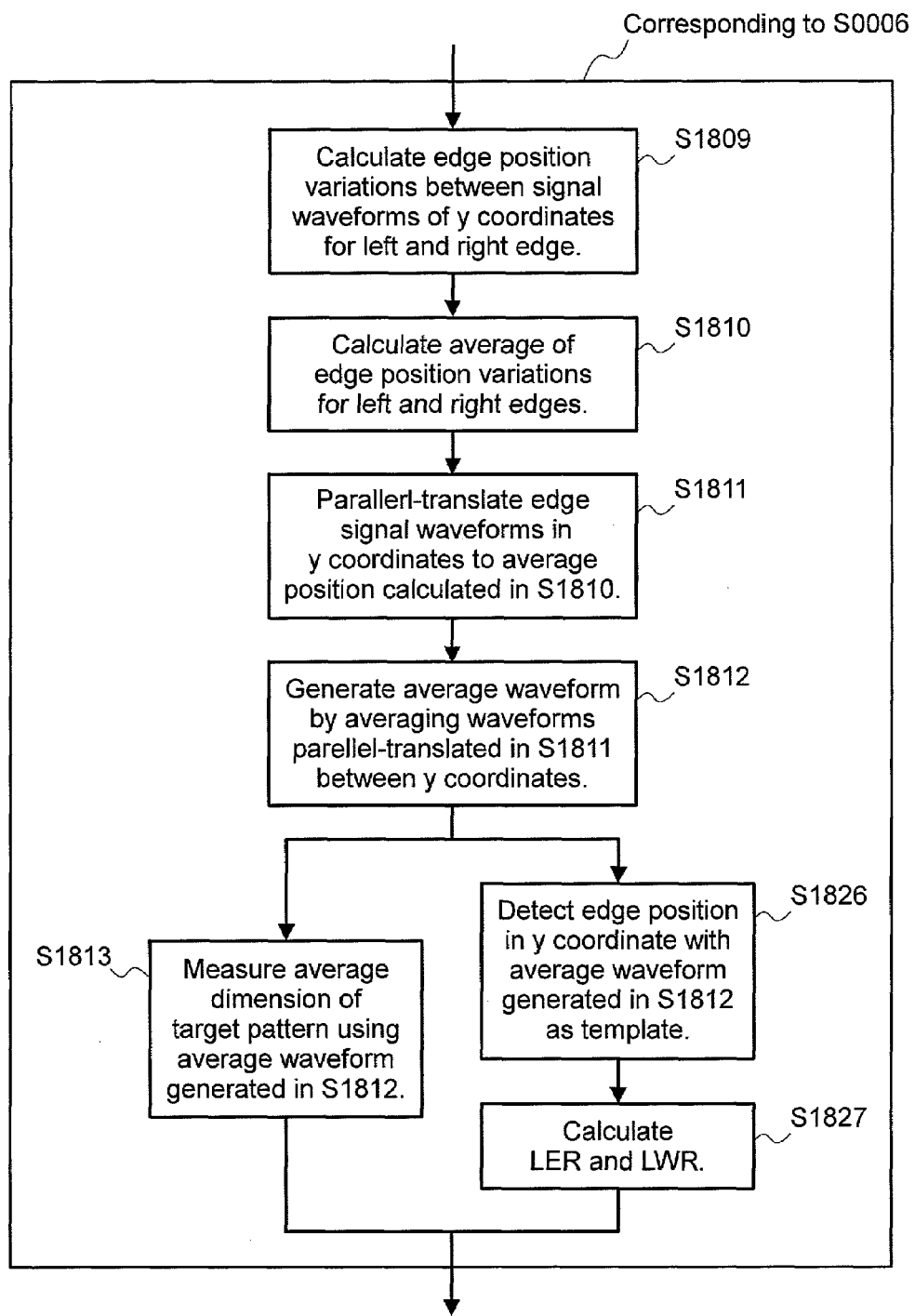
FIG. 18 is a flow chart illustrating a pattern measuring method according to a fourth modification of the first embodiment of the invention.

That is, as shown in the flow chart of FIG. 18, edge position variations of the signal waveforms of the y coordinates are calculated at Step S1809, an average of the calculated edge position variations is calculated (S1810), an edge waveform signal is parallel-translated to the calculated average position (S1811), an average waveform is generated by averaging the signal waveforms (S1812), and pattern dimension measurement is carried out using the average waveform (S1813).

On the other hand, with the edge waveform of the obtained average waveform as a template, when edge position deviation of y coordinates in the original image is calculated (S1826) and LER or LWR is calculated using the calculated edge position deviation (S1827), since the edge waveform having low noise and a high S/N ratio can be used for the template, it is possible to measure LER or LWR stably.

With this process of the fourth modification, it is possible to calculate the average waveform at the average position without deteriorating a signal waveform used for pattern dimension measurement and shape information extraction. Pattern dimension measurement with higher precision can be carried out using the average waveform having a low noise component obtained so (S1813).

FIG. 19 shows an example of a result in the pattern measuring method according to the fourth modification, specifically showing an image as a combination of an average waveform and a result of an edge position variation coordinate calculated with the average waveform as a template in comparison with an original image. Since the combined image has noise lower than the original image, it is possible to clearly indicate variation of a pattern shape and hence easily confirm a pattern shape state. Although not shown in FIG. 19, measured edge positions in the y coordinates may be overlapped on the combined image.

These first to fourth modifications in first embodiment may be used in combination with second and third embodiments which will be described below.

Second Embodiment

Next, a high precision measurement method considering a pattern cubic shape and a cubic shape estimation method according to a second embodiment of the invention will be described with reference to FIG. 7.

The deformation of a signal waveform by the noise removing process as shown in FIGS. 5 and 6 may make it difficult to obtain pattern cubic shape information of the signal waveform as well as a result of edge position detection.

For example, although Non-Patent Document 3 discloses a dimension measurement method considering a sectional shape of a pattern with attention paid to a relationship between a pattern shape and a waveform, there is a case where sufficient performance can not be obtained if a measurement target image has a low S/N ratio, as disclosed in [Villarrubia et al.]. In this manner, when the noise removing process as shown in FIG. 5 or 6 is performed for the SEM image, since an SEM signal waveform used for measurement is varied, it is difficult to obtain cubic shape information of the target pattern from the shape of the SEM signal waveform.

On the contrary, in the second embodiment of the invention, as shown in FIG. 7, measurement with high precision is realized using an average waveform generated by the noise removing process considering roughness and an SEM simulation. To begin with, as shown in FIG. 7A, an SEM waveform library is constructed in advance through an off-line simulation. First, simulation conditions are set from a supposed variation range of a target shape and image acquisition conditions (acceleration voltage of electron beam irradiation or the like) in a CD-SEM (S7001), and then an SEM simulation for various pattern shapes and dimensions is made under the set conditions (S7002).

The various pattern shapes include shape features to be measured as a target pattern, for example, a side wall inclination angle, roundness of a top or bottom portion, etc. In a process for an object to be measured, if a shape prone to be varied is known (for example, if a top corner is prone to be rounded), it is important to consider its shape variation. Considering a range for such shape parameters which may occur in an actual process, a simulation is made in a range covering this range for such shape parameters. Thereafter, a library 304 of an SEM signal waveform is constructed using a result of this simulation (S7003).

In measurement, an SEM image is acquired under the same conditions as the construction of the SEM waveform library in an order such as S0001 to S0007 shown in FIG. 1A. At this time, similar to steps from S0009 to S0012 in the first embodiment, a detailed step corresponding to the measurement step (S0006) shown in FIG. 1B includes calculating edge position variations (S7009), calculating an average of the edge position variations from the calculated edge position variations (S7010), parallel-translating an edge signal waveform to the calculated average position (S7011), and generating an average waveform with reduced noise, considering variation of the pattern edge positions, by generating the average waveform (S7012). The generated average waveform is compared with data of the SEM waveform library 304 constructed through the simulation, and a result of estimation of dimensions and sectional shapes of the measurement target pattern is obtained from input shape data having simulation conditions used to generate the waveform closest to the average waveform (S7013).

Figure 9:
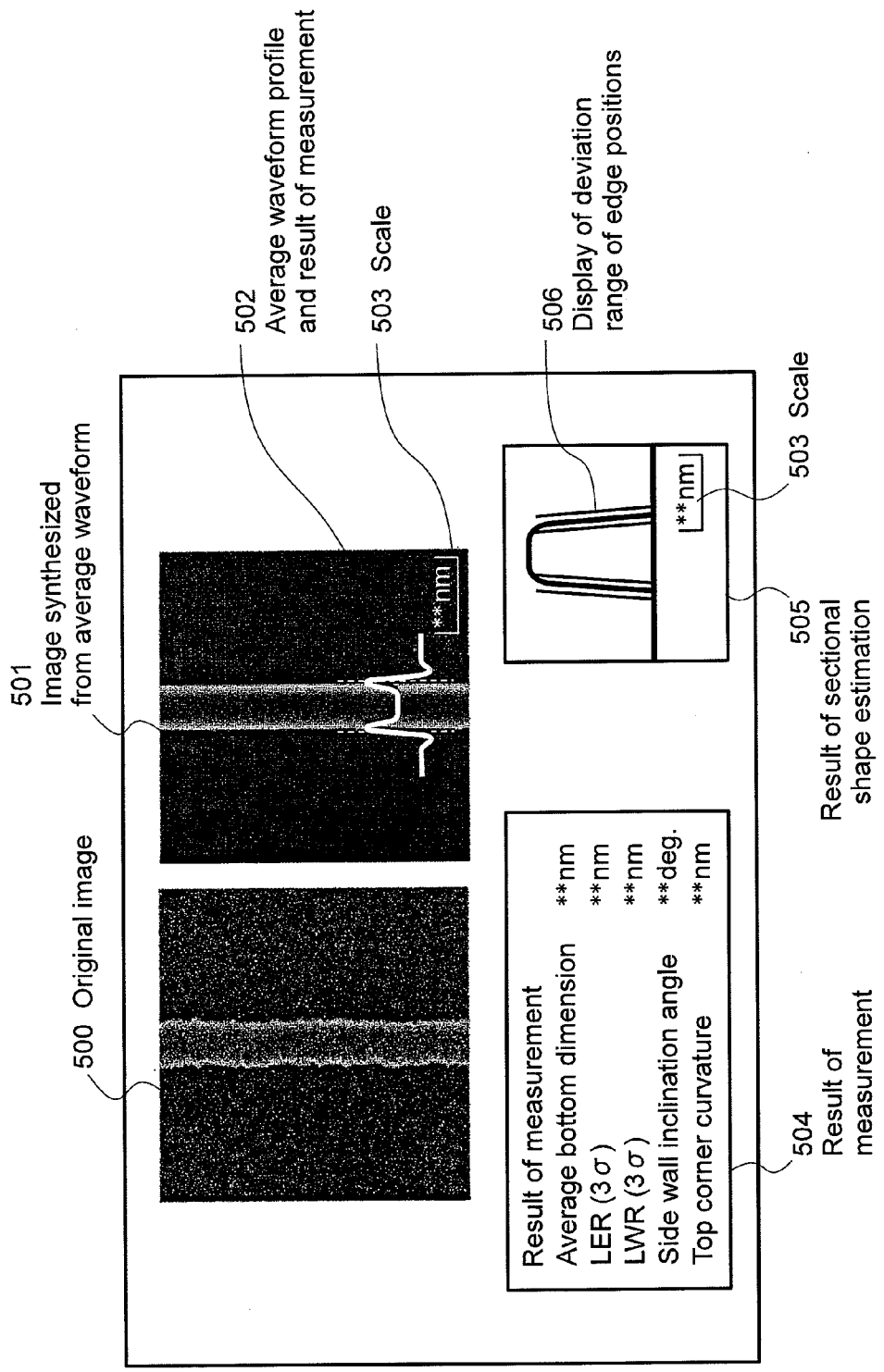
FIG. 9 is a front view of a screen showing a result in the pattern measuring method according to the second embodiment of the invention.

FIG. 9 shows an example of a screen showing a result in the pattern measuring method according to the second embodiment. In the example of FIG. 9, an original image 500 used for estimation and an image 501 synthesized from the average waveform are displayed. The image synthesized from the average waveform has noise lower than the original image and has no LER/LWR in average dimensions, and accordingly is clearer than the original image, thereby helping to confirm a target pattern state. In addition, when an average waveform profile and a dimension measurement result (for example, bottom dimensions) 502 and a scale 503 showing a magnification are indicated on the synthesized image of the average waveform, the measurement results can be confirmed more easily and conveniently. Numerical values 504 of the measurement results are indicated in a left and bottom portion of the screen and a sectional shape 505 estimated in the second embodiment is indicated in a right and bottom portion of the screen. It is convenient that the same scale 503 as the image is indicated for the result of the sectional shape estimation. In addition, a difference range 506 of edge positions by LER estimated from the original image may be indicated. A method of measuring LER with high precision has been already described in the fourth modification of the first embodiment.

In the second embodiment, like the first embodiment, it is possible to solve the problem occurred in the conventional smoothing process. That is, since the average waveform generating process of the invention considering any roughness of a sample not only reduces noise but also calculates a waveform at an average position in an image to be processed with a signal waveform of an edge kept unchangeable, it is possible to reduce a dimension variation component, which is not derived from an original pattern but may occur when the smoothing process is performed similar to the related art, and carry out measurement safely with high precision and high sensitivity. In particular, when a cubic shape of a target pattern is estimated from the waveform shape as in the second embodiment, it is very important to prevent a waveform from being varied due to the smoothing.

By using the second embodiment of the invention, although an SEM image having a low S/N ratio is used for a material having low resistance to electron beam irradiation, it is possible to realize the estimation of stable measurement with high precision and the cubic shape with relatively low amount of electron irradiation, that is, with less damage. As a result, it is possible to detect variation of a semiconductor process with high sensitivity.

In addition, in the second embodiment shown in FIG. 7, one average waveform obtained by the process of the second embodiment is compared with the simulation library (S7013). For the comparing process (S7013) with the simulation library, since it is required to estimate many parameters used for the simulation by the comparison of the average waveform with the simulation library, it takes a relatively long time to perform the comparing process.

The related art requires the same process for a plurality of waveforms in an image in order to calculate an average dimension of a pattern having roughness, but, with the second embodiment of the invention, since Step S7013 may be performed for only one waveform reflecting the overall average shape and dimension in the image, it is possible to significantly reduce calculation time.

Like the first embodiment, the number of images used for process is not necessarily one, but it should be understood that more images obtained by dividing and picking up an image on the same edge of a sample into two or more may be used. In this case, since the amount of used signal increases, it is possible to obtain a higher noise reduction effect.

Although the second embodiment is described using the secondary electron image of SEM, the signal used may be reflected electrons. Alternatively, the system may use FIB using light ions instead of an electron beam. Using the FIB, since a scattering angle in a solid is relatively small, it is possible to carry out measurement with high resolution power.

First Modification of Second Embodiment

In a first modification of the second embodiment, a method of making the cubic shape estimation method of the second embodiment more precise will be described with reference to FIG. 17. As shown in the third modification of the first embodiment, when the one-dimensional filter is applied to each signal waveform of a y coordinate, it is possible to remove noise without being affected by variation of neighboring edge positions. The first modification of the second embodiment provides a method of improving stability and precision of the cubic shape estimation method of the second embodiment by applying a smoothing process by the one-dimensional filter.

The upper side of FIG. 17 shows the second embodiment to compare an SEM signal waveform with a waveform of the SEM waveform simulation library to find a matching waveform. On the contrary, in the first modification of the second embodiment, as shown in the lower side of FIG. 17, the same one-dimensional smoothing filter is applied to both of the SEM signal waveform and the simulation library, and waveforms with noises removed are compared with each other. The smoothing process varies an edge waveform shape as described above. However, in the first modification of the second embodiment, since the same smoothing process is also applied to the simulation library and accordingly the simulation library is likely varied, there is no problem in estimating a cubic shape even when a waveform shape is varied after noises are removed. In this manner, by applying the same one-dimensional smoothing process to both of the signal waveform and the simulation waveform, it is possible to make the pattern dimension measurement and the cubic shape estimation of the second embodiment more precise.

Third Embodiment

Next, a method of evaluating a semiconductor manufacturing process using pattern shape information according to a third embodiment will be described with reference FIGS. 10 and 11.

As described above, the deformation of a signal waveform by the noise removing process as shown in FIGS. 5 and 6 may make it difficult to obtain pattern cubic shape information of the signal waveform as well as a result of edge position detection.

Figure 8:
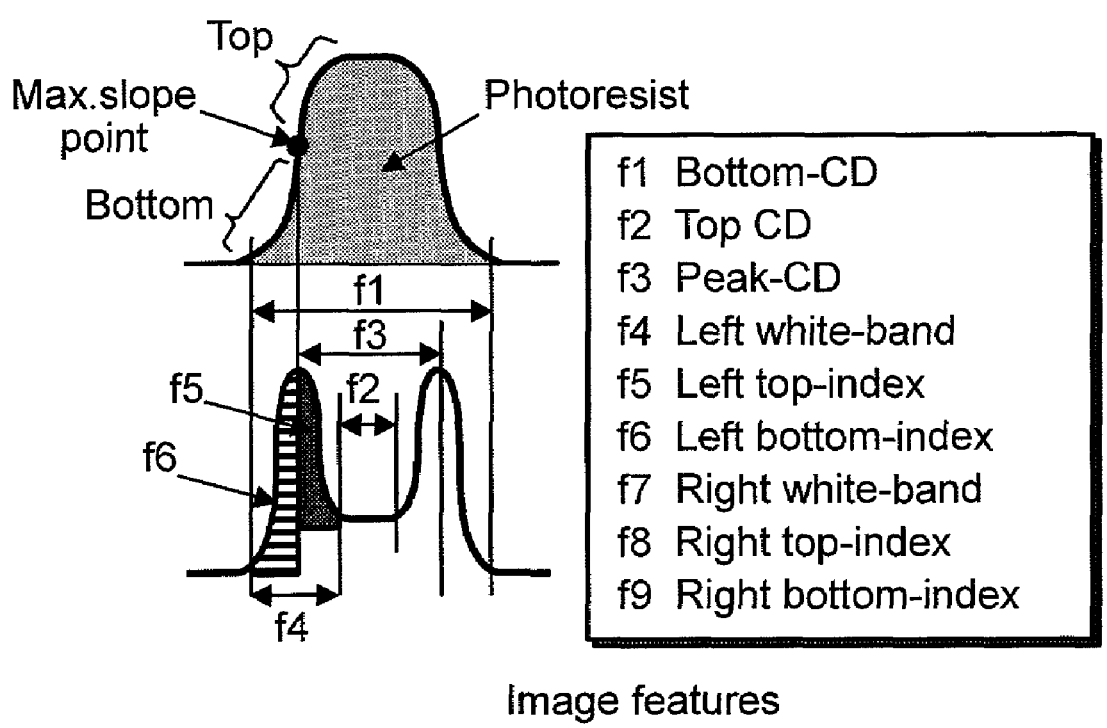
FIG. 8 is a known view illustrating various image features in an SEM signal waveform.

Non-Patent Document 5 discloses a method of dividing an SEM signal waveform into a plurality of regions and extracting pattern shape information as shown in FIG. 8. In this case, although it is important to remove noises in order to obtain a stable result, if the process as shown in FIG. 5 or 6 is performed, since a waveform is unstably varied due to an effect of roughness of a pattern, it is difficult to obtain high sensitivity to cubic shape variation of the pattern.

Figure 10:
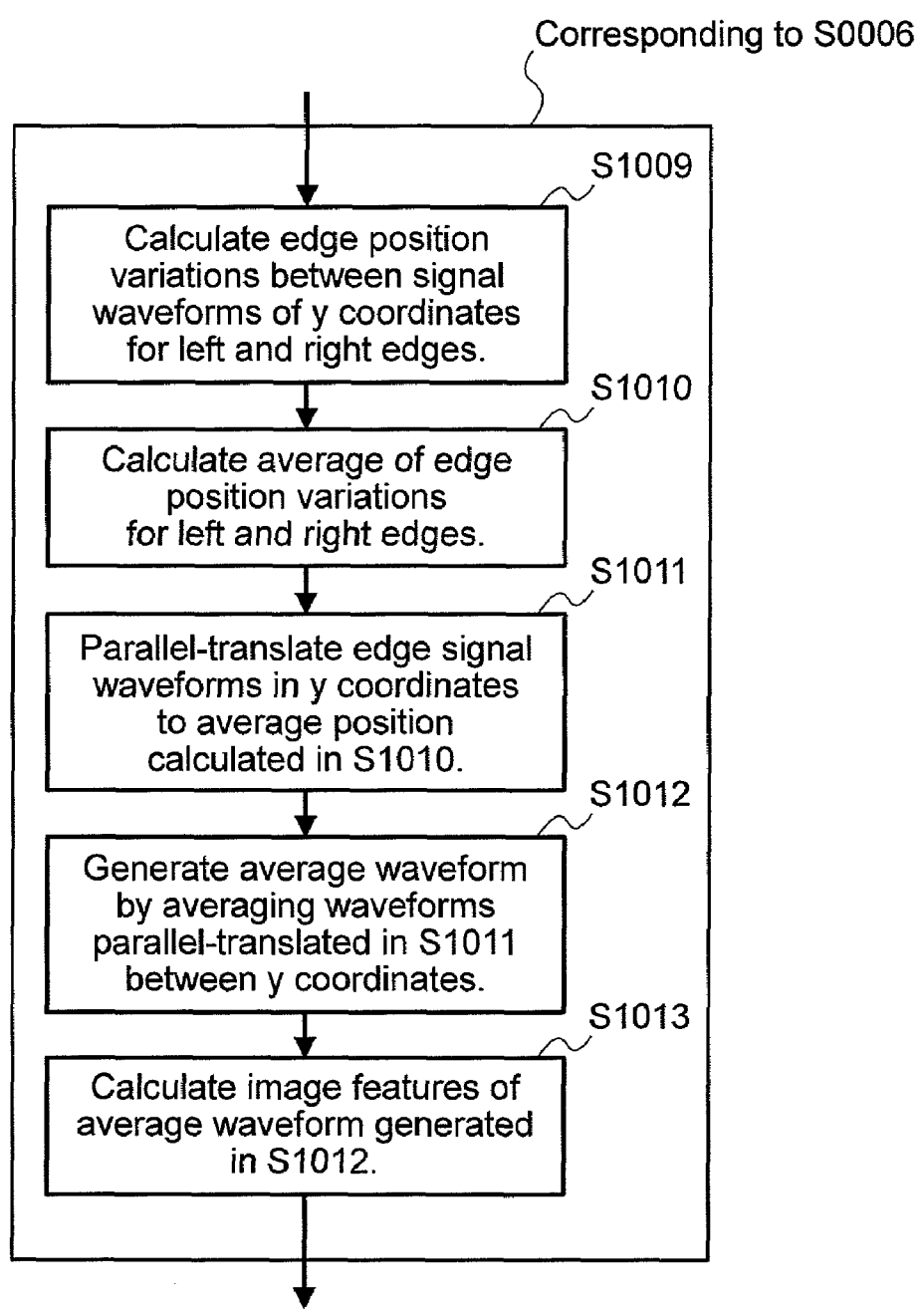
FIG. 10 is a flow chart illustrating calculation of an image feature in a pattern measuring method according to a third embodiment of the invention.

In the third embodiment, as shown in FIG. 10, high precision image features are calculated using an average waveform generated by a noise removing process considering roughness and an SEM simulation, and a monitor of an exposure apparatus using the obtained high precision image features. An order of SEM image acquisition is the same as the order shown in FIG. 1A. Using the obtained SEM image, edge position variations are calculated (S1009) in an order of Steps S1009 to S1012 shown in FIG. 10, like the order of Steps S0009 to S0012 for measurement shown in FIG. 1B of the first embodiment, an average of the calculated edge position variations is calculated based on the calculated result (S1010), an edge signal waveform is parallel-translated to the calculated average position (S1011), and an average waveform is generated from the parallel-translated waveform (S1012). Accordingly, an average waveform with noises removed can be generated with a waveform shape kept unchangeable.

Next, in Step S1013, image features varying depending on a pattern shape are calculated from the obtained average waveform. The image features may be obtained using, for example, a method of dividing an SEM signal waveform into a plurality of regions and extracting pattern shape information from each region, as shown in FIG. 8, which is disclosed in [Shishido et al] authored by the present inventors and JP-A-2003-173948.

As shown in FIG. 10, by using the average waveform having reduced noise with a signal waveform shape kept unchangeable, it is possible to calculate high sensitive and stable image features as compared to the related art. Now, a monitoring method of an exposure apparatus using the high sensitive and stable image features will be described with reference to FIG. 11. This monitoring method includes a database preparation procedure (FIG. 11A) to record a relationship between process conditions and image features indicating cubic shapes of a pattern generated under the process conditions in a database in advance, and an exposure apparatus parameter estimation procedure (FIG. 11B) to estimate variation of the process conditions using the database.

Figure 11A:
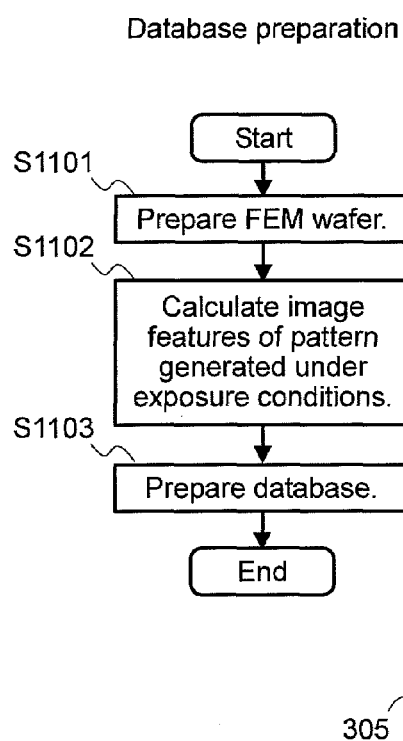
FIG. 11A is a flow chart illustrating preparation of a database in the pattern measuring method according to the third embodiment of the invention.
Figure 11B:
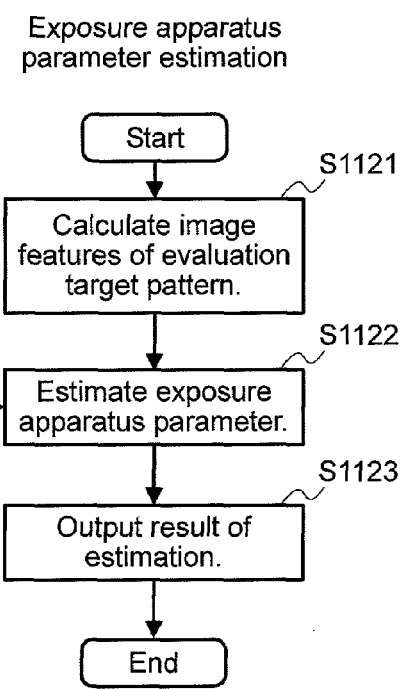
FIG. 11B is a flow chart illustrating estimation of an exposure apparatus parameter in the pattern measuring method according to the third embodiment of the invention.

In the database preparation procedure, as shown in FIG. 11A, first, a FEM (Focus Exposure Matric) wafer exposed with focus and exposure amount, as main exposure conditions, changed for each chip is generated (S1101). Next, in Step S1102, SEM image acquisition and image feature calculation of patterns generated under respective conditions are made in the order of Step S1009 to S1013 shown in FIG. 10. Finally, a database 305 is prepared using a relationship between the image features calculated in accordance with the method of the invention and the conditions (focus and exposure amount) of the exposure apparatus (S1103). In actual process management, based on the order shown in FIG. 11B, image features of an evaluation target pattern are calculated in the order shown in FIG. 10 (S1121), and the calculated image features are compared with image features recorded in the database 305 to estimate variation of the conditions of the exposure apparatus (S1122) and output a result of the estimation (S1123).

In the third embodiment, like the first and second embodiments, it is possible to solve the problem occurred in the conventional smoothing process. That is, since the average waveform generating process of the invention considering any roughness of a sample not only reduces noise but also calculates a waveform at an average position in an image to be processed with a signal waveform of an edge kept unchangeable, it is possible to reduce a signal waveform variation component, which is not derived from an original pattern but may occur when the smoothing process is performed similar to the related art, and calculate image features depending on a target pattern shape with high precision and high sensitivity.

When information related to a cubic shape of a target pattern is extracted from the waveform shape as in the third embodiment, it is very important to prevent a waveform from being varied due to the smoothing.

By using the third embodiment of the invention, although an SEM image having a low S/N ratio is used for a material having low resistance to electron beam irradiation, it is possible to extract cubic shape information of a pattern stably and with high precision with relatively low amount of electron irradiation, that is, with less damage. As a result, it is possible to detect variation of a semiconductor process with high sensitivity.

Like the first embodiment, the number of images used for process is not necessarily one, but it should be understood that more images obtained by dividing and picking up an image on the same edge of a sample into two or more may be used. In this case, since the amount of used signal increases, it is possible to obtain a higher noise reduction effect.

Although the second embodiment is described using the secondary electron image of SEM, the signal used may be reflected electrons. Alternatively, the system may use FIB using light ions instead of an electron beam. Using the FIB, since a scattering angle in a solid is relatively small, it is possible to carry out measurement with high resolution power.

Fourth Embodiment

Next, a pattern measuring method of generating an average waveform in a way different from the first embodiment will be described with reference to FIGS. 20 to 24.

Figure 20A:
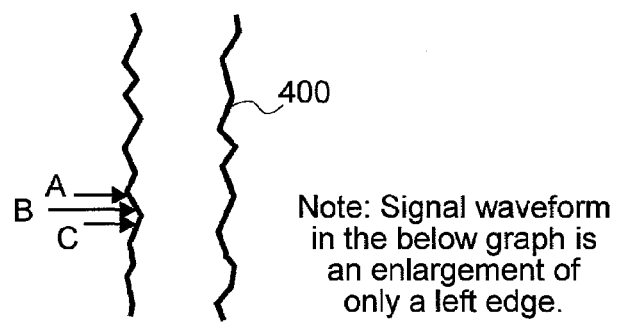
FIG. 20A is a schematic plan view of a pattern to be measured.
Figure 20B:
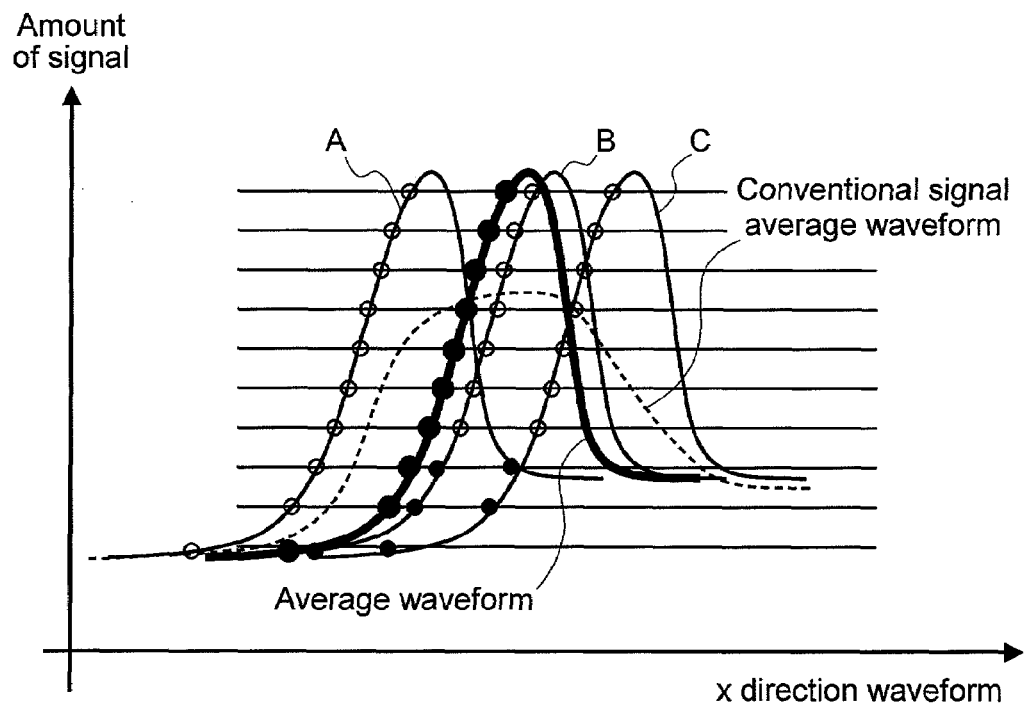
FIG. 20B is a signal waveform diagram showing an average waveform generating process in a pattern measuring method according to a fourth embodiment of the invention.

FIG. 20 is a view for explaining the concept of the fourth embodiment. Although a waveform having no noise is illustrated in FIG. 20 in order to clarify an effect, this waveform is in actuality a waveform having any noises. Conventional signal waveforms as indicated by dotted line in FIGS. 20A and 20B are the same as shown in FIG. 2. On the contrary, in the fourth embodiment, an average waveform is generated by calculating an average position of signal waveforms with the same amount of signal. In FIG. 20B, points at which signal waveforms indicated by thin lines have the same amount of signal (outline points indicated on the same horizontal line) are calculated, and, when average coordinates (black points) are interconnected, an average waveform (thick line) moved to an average position of an original waveform can be obtained with an original signal waveform shape kept unchangeable.

Figure 21:
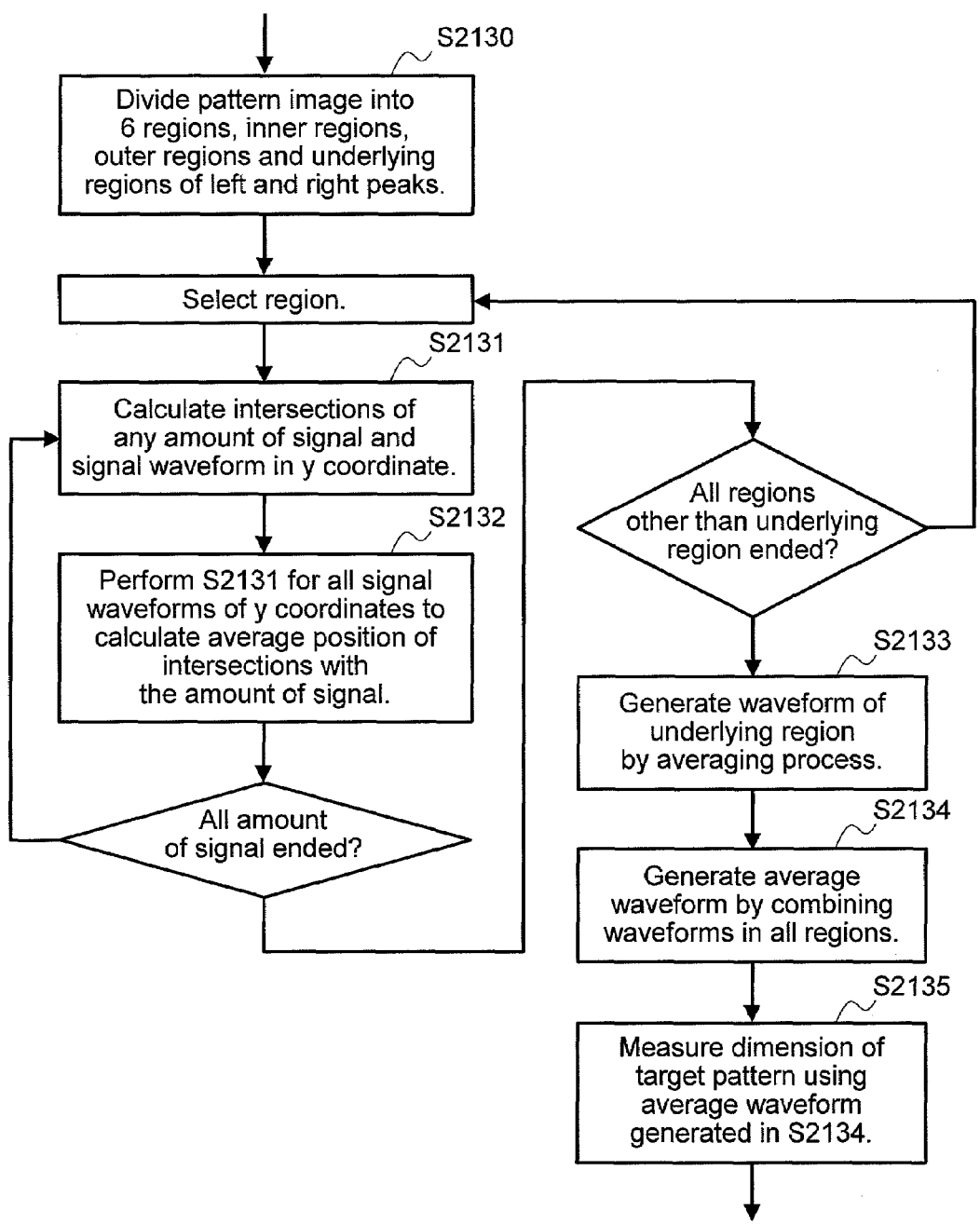
FIG. 21 is a flow chart illustrating the pattern measuring method according to the fourth embodiment of the invention.
Figure 22:
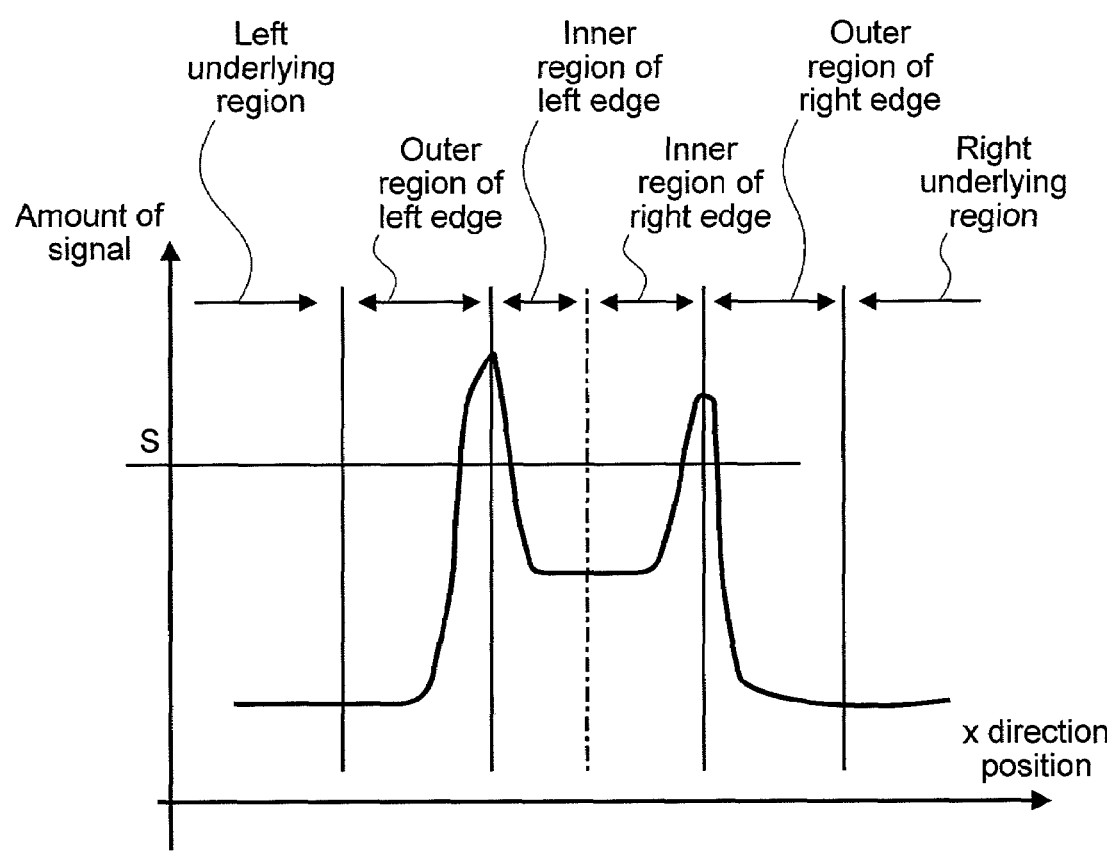
FIG. 22 is a signal waveform diagram explaining region division in the pattern measuring method according to the fourth embodiment of the invention.

FIG. 21 shows an actual order. In general, an SEM signal waveform used for line pattern measurement has two or more corresponding coordinates. Although only the left sides of edge waveform peaks are illustrated in FIG. 20 for the sake of clarity, the right side and a side of another edge waveform peak have points having the same amount of signal. So, as shown in FIG. 22, first, a signal waveform is divided into 6 regions, that is, peak inner regions, peak outer regions, and underlying regions of left and right edges (S0030). Next, for the regions other than the underlying regions, positions having any amount of signal in the signal waveform of a y coordinate are calculated (S0031).

Figure 23:
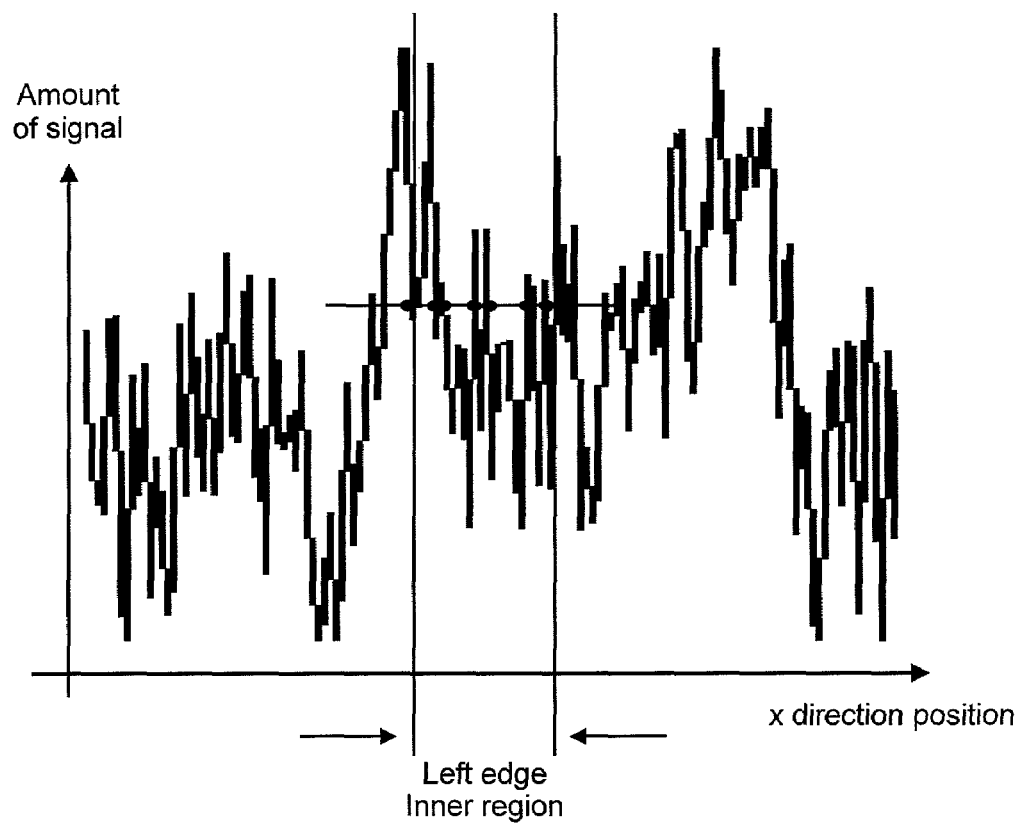
FIG. 23 is a signal waveform diagram showing a region in a left edge in the pattern measuring method according to the fourth embodiment of the invention.

Although FIG. 20 shows a waveform having no noise, since an actual waveform has any noise as shown in FIG. 23, there is in general a plurality of intersections with any amount of signal. However, if noises are random, an average of the plurality of intersections may be close to a coordinate having the amount of signal. Accordingly, all the plurality of intersections to be calculated is obtained in Step S0031. Next, this process is performed for all signal waveforms to calculate an average position (S0032).

Figure 24:
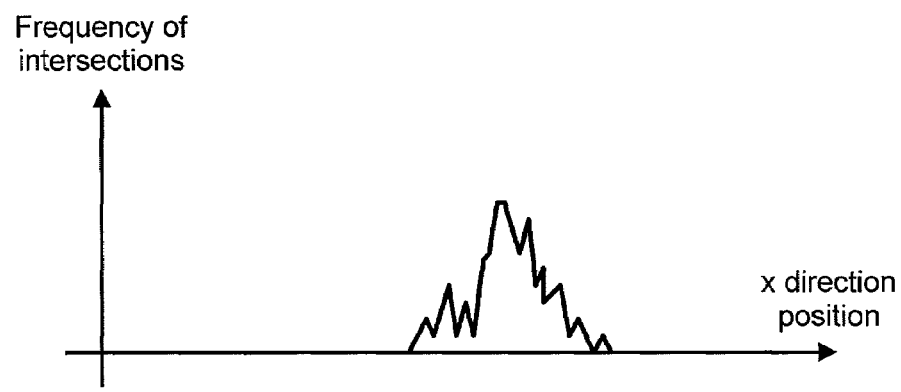
FIG. 24 is a view explaining the pattern measuring method according to the fourth embodiment of the invention, showing a histogram indicating frequency of coordinates of all intersection points obtained for one signal in the signal waveform diagram of FIG. 23.

A histogram for coordinates of all intersections obtained for one amount of signal has a distribution with any deviation, as shown in FIG. 24. This deviation includes deviation of edge positions of a measurement object and deviation by noises. If data are sufficiently obtained, by estimating an average position of these data, it is possible to restore an original signal waveform with deviation of both of the edge positions and noises removed. Instead of a simple mean value, a median of coordinates or the maximum frequency of the histogram (which may be smoothed) may be used, or any suitable method may be selected depending on the number of obtained data. Steps S0031 and S0032 are performed for all amount of signal and four regions of edge peaks. Since the underlying regions have no pattern, waveforms of the underlying regions are simply estimated by the signal averaging process similar to the conventional process (S0033).

The signal waveforms obtained in the regions are combined to generate an average waveform (S0034), and, like the first embodiment, an average dimension of a target pattern can be measured using the generated average waveform (S0035). With the fourth embodiment, like the first embodiment, it is possible to realize stable and highly precise measurement.

For the second and third embodiments, when the pattern dimension measurement, the cubic shape estimation or the calculation of image features related to the pattern shape is made using the average waveform generated by the method of the fourth embodiment instead of an average waveform with edge position variation, it is possible to attain the same effects as the first to third embodiments.

Fifth Embodiment

Figure 25A:
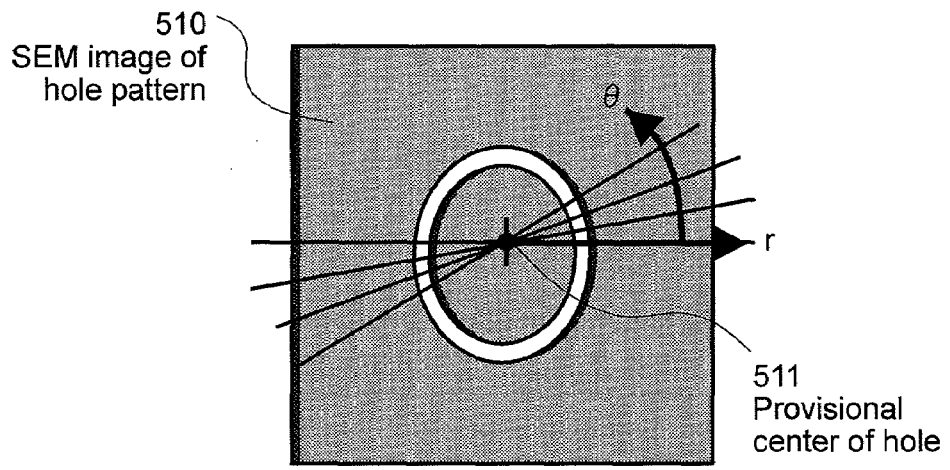
FIG. 25A is a view showing an SEM image with a hole pattern.

Next, a method of applying the above-described embodiments to a hole pattern will be described. If a measurement object is a hole pattern, since an edge of a hole is brightened like an edge of a line, an SEM image 510 of the hole pattern is as shown in FIG. 25A.

Figure 25B:
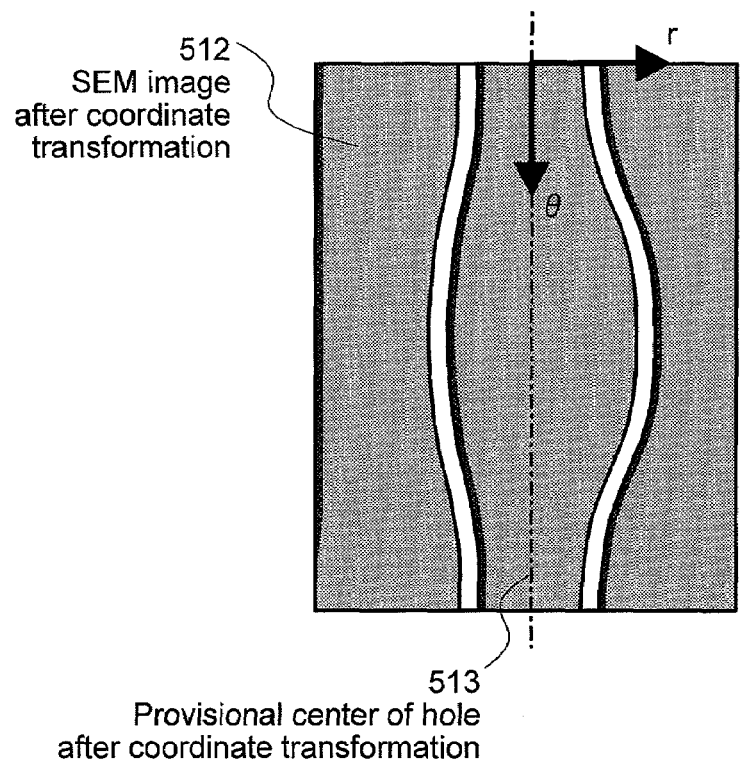
FIG. 25B is a view showing an image obtained by polar-transforming the SEM image with the hole pattern.

Hereinafter, an order of application of the invention to such an image will be described. First, a provisional center 511 of the hole is calculated in a conventional way. Here, low detection precision causes no problem. Next, on the basis of the calculated provisional center 511 of the hole, a radius direction r and an axis of an angle direction θ perpendicular to the radius direction r are determined as shown in FIG. 25A, and the SEM image 510 of the obtained hole pattern is polar-transformed to generate an SEM image 512 after the transformation as shown in FIG. 25B. At this time, a provisional center 513 of the hole after the transformation becomes a straight line as indicated by a dotted line in FIG. 25B.

As shown in FIG. 25B, the image after the polar transformation becomes the same image as the line pattern shown in FIG. 4C or the like. In this manner, if an image having a hole pattern can be transformed to have the same shape as a line pattern through coordinate transformation, it is possible to apply all the above-described embodiments to this image in the same way. If edge positions of the hole can be determined with higher precision after the application of the above embodiments, when a central position of the hole or a hole diameter is again calculated later, it is possible to realize hole measurement with high precision as compared with the conventional process.

With the fifth embodiment, like the first embodiment, it is possible to realize stable and highly precise measurement. For the second and third embodiments, when the pattern dimension measurement, the cubic shape estimation or the calculation of image features related to the pattern shape is made using the average waveform generated by the method of the fifth embodiment instead of an average waveform with edge position variation, it is possible to attain the same effects as the first to fourth embodiments.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description and all changes which come within the meaning and range of equivalency of the claims are therefore intended to be embraced therein.

What is claimed is:

1. A method of measuring pattern dimensions, comprising the steps of:
    obtaining an image of a region on a sample in which a measurement target pattern is formed, by irradiating and scanning the region with a focused charged particle beam and detecting secondary charged particles generated from the sample;
    forming an added signal waveform of the measurement target pattern by adding plural signal waveforms of the obtained image to a direction perpendicular to the scanning direction of the charged particle beam; and
    obtaining dimension information of the measurement target pattern from the added signal waveform of the measurement target pattern,
    wherein, in the step of forming an added signal waveforms, the plural signal waveforms to be added are corrected in deviation of the waveforms corresponding to edge positions caused by edge portion roughness of the measurement target pattern.

2. The method according to claim 1,
    wherein the correction of signal waveform edge position deviation due to roughness of an edge of the measurement target pattern is made by obtaining edge position deviations of the measurement target pattern for the signal waveforms to be added, obtaining an average of the obtained edge position deviations of the measurement target pattern for the signal waveforms, and correcting the edge position deviations of the measurement target pattern for the signal waveforms with respect to the obtained average.

3. The method according to claim 1,
    wherein the correction of signal waveform edge position deviation due to roughness of an edge of the measurement target pattern is made by acquiring a signal waveform having a high S/N ratio of the measurement target pattern from an image obtained by scanning positions other than the measurement position with more charged particle beam than that of the measurement position, and correcting and adding the signal waveform edge position deviation due to roughness of the edge of the measurement target pattern, with the acquired signal waveform having the high S/N ratio as a template, to obtain the addition signal of the measurement target pattern.

4. The method according to claim 1,
    wherein the correction of signal waveform edge position deviation due to roughness of an edge of the measurement target pattern is made by removing noises by application of a smoothing filter to the signal waveform of the image in the scanning direction particle beam, obtaining edge positions of the measurement target pattern for signal waveforms with noises removed, obtaining an average of the obtained edge positions of the measurement target pattern for signal waveforms with noises removed, obtaining edge position deviations of the measurement target pattern for signal waveforms with noises removed with respect to the obtained average, and correcting the signal waveform of the image in the scanning direction of the charged particle beam based on the obtained edge position deviations.

5. The method according to claim 1,
    wherein a sectional shape of the measurement target pattern is estimated by comparing the dimension information of the measurement target information obtained from the waveform of the addition signal of the measurement target pattern and the waveform of the addition signal with a relationship between a previously obtained pattern shape and a signal waveform shape of the image obtained by irradiating and scanning the pattern with the charged particle beam.

6. The method according to claim 5,
    wherein information of the estimated sectional shape of the measurement target pattern is displayed on a screen along with the dimension information of the measurement target pattern and the obtained image of the region in which the measurement target pattern is formed.

7. An apparatus for measuring pattern dimensions, comprising:
    an image acquisition unit that includes a charged particle beam irradiator and a secondary charged particle detector, and obtains an image of a region on a sample in which an measurement target pattern is formed, by irradiating and scanning the region with a charged particle beam formed by the charged particle beam irradiator and detecting secondary charged particles generated from the sample by the irradiation and scanning of the charged particle beam; and
    an image processing unit that obtains dimension information of the measurement target pattern by processing the image obtained by the image acquisition unit,
    wherein the image processing unit includes a signal waveform processor that forms an added signal waveform of the measurement target pattern by adding plural signal waveforms of the obtained image to a direction perpendicular to the scanning direction of the charged particle beam, and a pattern dimension information extracting part that obtains dimension information of the measurement target pattern from the added signal waveform of the measurement target pattern formed by the signal waveform processor,
    wherein said signal waveform processor corrects deviations of the signal waveforms corresponding to edge positions of the measurement target pattern caused by edge portion roughness of the measurement target pattern.

8. The apparatus according to claim 7,
    wherein the correction of signal waveform edge position deviation due to roughness of an edge of the measurement target pattern in the signal waveform processor is made by obtaining edge positions of the measurement target pattern for the signal waveforms to be added, obtaining an average of the obtained edge positions of the measurement target pattern for the signal waveforms, and correcting edge position deviations of the measurement target pattern for the signal waveforms with respect to the obtained average.

9. The apparatus according to claim 7,
    wherein the correction of signal waveform edge position deviation due to roughness of an edge of the measurement target pattern in the signal waveform processor is made by acquiring a signal waveform having a high S/N ratio of the measurement target pattern from an image obtained by scanning positions other than the measurement position with more charged particle beam than that of the measurement position, and correcting and adding signal waveform deviation due to roughness of the edge of the measurement target pattern, with the acquired signal waveform having the high S/N ratio as a template, to obtain the addition signal of the measurement target pattern.

10. The apparatus according to claim 7, wherein the correction of signal waveform edge position deviation due to roughness of an edge of the measurement target pattern in the signal waveform processor is made by removing noises by application of a smoothing filter to the signal waveform of the image in the scanning direction particle beam, obtaining edge positions of the measurement target pattern for signal waveforms with noises removed, obtaining an average of the obtained edge positions of the measurement target pattern for signal waveforms with noises removed, obtaining edge position deviations of the measurement target pattern for signal waveforms with noises removed with respect to the obtained average, and correcting the signal waveform of the image in the scanning direction of the charged particle beam based on the obtained edge position deviations.

11. The apparatus according to claim 7, wherein the pattern dimension information extracting part estimates a sectional shape of the measurement target pattern by comparing the dimension information of the measurement target pattern obtained in the signal waveform processor from the waveform of the addition signal of the measurement target pattern and the waveform of the addition signal with a relationship between a previously obtained pattern shape and a signal waveform shape of the image obtained by irradiating and scanning the pattern with the charged particle beam.

12. The apparatus according to claim 11, further comprising a display unit having a display screen, wherein information of the sectional shape of the measurement target pattern estimated in the pattern dimension information extracting part, the dimension information of the measurement target pattern, and the image of the region in which the measurement target pattern is formed, the image being obtained in the image acquisition unit, are displayed on the display screen of the display unit.

13. A method of measuring dimensions of a pattern having a column-like edge, comprising the steps of:

obtaining an image of a region in which the pattern having the column-like edge on a sample is formed, by irradiating and scanning the region with a focused charged particle beam and detecting secondary charged particles generated from the sample;

obtaining an addition signal of the pattern by adding a signal waveform of the image in a scanning direction of the charged particle beam to a signal waveform in a direction perpendicular to the scanning direction; and obtaining dimension information of the pattern from a waveform of the obtained addition signal of the pattern, wherein the step of obtaining dimension information of the pattern comprises assuming a point existing within the column of the pattern having the column-like edge as a reference point, performing coordinate-transformation for a charged particle beam image using coordinates of a distance from the reference point and a rotation direction around the reference point, and obtaining the dimension information of the pattern using an image after the transformation.

14. An apparatus for measuring dimensions of a pattern having a column-like edge, comprising:

an image acquisition unit that includes a charged particle irradiator and a secondary charged particle detector, and obtains an image of a region in which the pattern having the column-like edge on a sample is formed, by irradiating and scanning the region with a charged particle beam focused by the charged particle irradiator and detecting secondary charged particles generated from the sample to which the focused charged particle beam is irradiated and scanned; and an image processing unit that obtains dimension information of the pattern by processing the image obtained by the image acquisition unit, wherein the image processing unit includes a signal waveform processor that forms an added signal waveform of the measurement target pattern by adding plural signal waveforms of the obtained image to a direction perpendicular to the scanning direction of the charged particle beam, and a pattern dimension information extracting part that obtains dimension information of the measurement target pattern from the added signal waveform of the measurement target pattern formed by the signal waveform processor, and the pattern dimension information extracting part assumes a point existing within the column of the pattern having the column-like edge as a reference point, performs coordinate-transformation for a charged particle beam image using coordinates of a distance from the reference point and a rotation direction around the reference point, and obtains the dimension information of the pattern using an image after the transformation.

* * * * *